US012230405B1

(12) United States Patent
Josephson et al.

(10) Patent No.: US 12,230,405 B1
(45) Date of Patent: *Feb. 18, 2025

(54) MACHINE REASONING AS A SERVICE

(71) Applicant: IQVIA Inc., Parsippany, NJ (US)

(72) Inventors: Scott Josephson, Raleigh, NC (US); Gary Shorter, Cary, NC (US)

(73) Assignee: IQVIA Inc., Parsippany, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/443,857

(22) Filed: Feb. 16, 2024

Related U.S. Application Data

(63) Continuation of application No. 18/180,209, filed on Mar. 8, 2023, now Pat. No. 11,908,587, which is a continuation of application No. 17/374,650, filed on Jul. 13, 2021, now Pat. No. 11,610,690.

(51) Int. Cl.
| | | |
|---|---|---|
| *G06F 16/901* | (2019.01) | |
| *G06F 16/903* | (2019.01) | |
| *G06F 40/30* | (2020.01) | |
| *G06N 5/02* | (2023.01) | |
| *G06N 5/04* | (2023.01) | |
| *G16H 50/70* | (2018.01) | |

(52) U.S. Cl.
CPC ......... *G16H 50/70* (2018.01); *G06F 16/9024* (2019.01); *G06F 16/90344* (2019.01); *G06F 40/30* (2020.01); *G06N 5/02* (2013.01); *G06N 5/04* (2013.01)

(58) Field of Classification Search
CPC .............. G16H 50/70; G06F 16/9024; G06F 16/90344; G06F 40/30; G06N 5/02; G06N 5/04
See application file for complete search history.

(56) References Cited

U.S. PATENT DOCUMENTS

| | | |
|---|---|---|
| 8,429,179 B1 | 4/2013 | Mirhaji |
| 9,760,564 B2 | 9/2017 | Byron et al. |
| 10,276,170 B2 | 4/2019 | Gruber et al. |
| 10,657,125 B1 | 5/2020 | Gautam et al. |
| 10,867,133 B2 | 12/2020 | Sweeney et al. |

(Continued)

OTHER PUBLICATIONS

International Search Report and Written Opinion in International Appln. No. PCT/US2022/072277, mailed on Jul. 25, 2022, 11 pages.

(Continued)

*Primary Examiner* — Jorge A Casanova
(74) *Attorney, Agent, or Firm* — Fish & Richardson P.C.

(57) ABSTRACT

Methods, systems, and apparatus, including computer programs encoded on computer storage media, for responding to a query. In some implementations, a computer obtains a query. The computer determines a meaning for each term in the query. The computer determines user data for the user that submitted the query. The computer identifies one or more ontologies based on the meanings for at least some of the terms. The computer identifies a knowledge graph based on the identified ontologies and the user data. The computer generates a response to the query by traversing a path of the identified knowledge graph to identify items in the knowledge graph based on the determined meaning for each of the terms. The computer generates path data that represents the path taken by the computer through the identified knowledge graph. The computer provides the generated response and the path data to the client device.

16 Claims, 8 Drawing Sheets

(56) References Cited

U.S. PATENT DOCUMENTS

| | | |
|---|---|---|
| 11,481,599 B2 | 10/2022 | You et al. |
| 11,610,690 B2 | 3/2023 | Josephson et al. |
| 11,908,587 B2 | 2/2024 | Josephson et al. |
| 2007/0294289 A1 | 12/2007 | Farrell |
| 2009/0076839 A1 | 3/2009 | Abraham-Fuchs et al. |
| 2014/0379755 A1 | 12/2014 | Kuriakose et al. |
| 2019/0057083 A1 | 2/2019 | Karres et al. |
| 2020/0257712 A1 | 8/2020 | Singh et al. |
| 2020/0320139 A1 | 10/2020 | Duishoev et al. |
| 2021/0064957 A1 | 3/2021 | You et al. |
| 2021/0254994 A1 | 8/2021 | Aït-Mokhtar et al. |
| 2022/0035998 A1 | 2/2022 | Galitsky |
| 2022/0238193 A1 | 7/2022 | Koc et al. |
| 2023/0017672 A1 | 1/2023 | Josephson et al. |
| 2023/0282368 A1 | 9/2023 | Josephson et al. |

OTHER PUBLICATIONS

Li et al., "Medical Knowledge Graph Construction and Applications," Dec. 19, 2019, Elsevier, 10 pages.
Santos et al., "Knowledge Graph To Interpret Clinical Proteomics Data," May 2022, Nature Biotechnology, 17 pages.

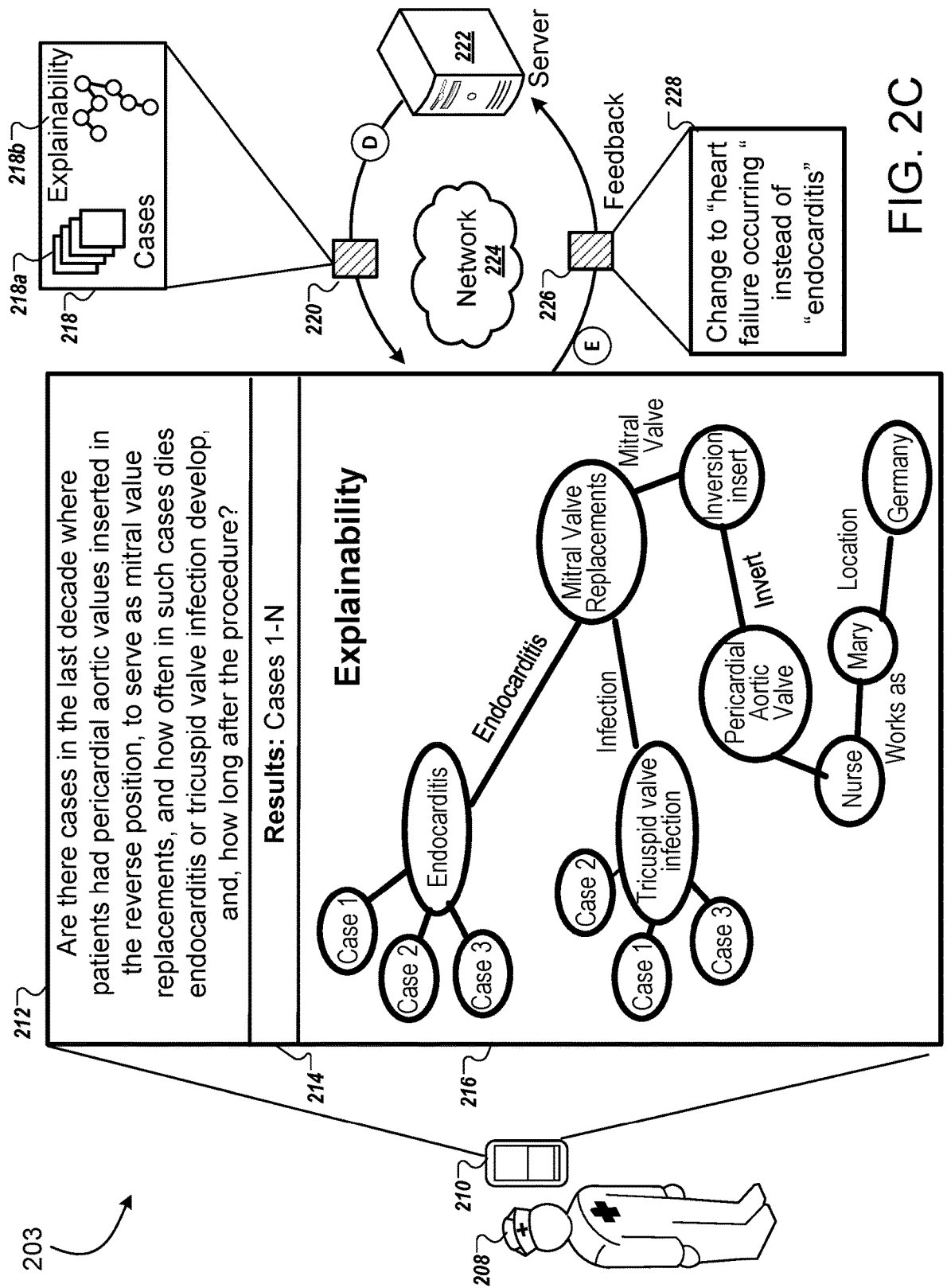

MACHINE REASONING AS A SERVICE

CROSS REFERENCE TO RELATED APPLICATIONS

This application is a continuation of U.S. patent application Ser. No. 18/180,209, filed Mar. 8, 2023, which is a continuation of U.S. patent application Ser. No. 17/374,650, filed Jul. 13, 2021, now U.S. Pat. No. 11,610,690, which is hereby incorporated by reference in its entirety.

TECHNICAL FIELD

This specification relates to predictive computing systems.

BACKGROUND

A clinical trial or program can be a single research study or multiple research studies that prospectively assigns human participants/subjects or groups of human subjects to one or more health-related interventions to evaluate the effects on health outcomes.

SUMMARY

As part of the healthcare process, physicians or other medical care providers may perform clinical trials, programs, and other activities to evaluate the safety and efficacy of a particular pharmaceutical drug or other medical treatment option. Conducting health-related clinical trials can help to identify medical treatment options, such as novel treatments, for improving overall patient health and reducing health system costs. Investigators that use a particular geographic site location to interact with study subjects generally conduct clinical trials and other controlled programs. In some instances, a physician for a patient can be associated with a clinical trial and the physician can refer a patient as a candidate for participation in a trial based on a diagnosed condition of the patient. An investigator, a geographic site location, or both, can form an entity that executes a program. The effectiveness of a trial program can depend on a variety of factors, such as obtaining a sufficient number of subjects that are suitable for participation in a trial, the accuracy of diagnosed conditions for each patient or subject in the program, or certain types of conditions that may prospectively affect a subject. In some cases, factors that impact the effectiveness of a clinical trial can vary depending on the treatment options being evaluated and the criteria that are associated with the trial.

Based on the above context, the techniques described in this specification enable a computing system that uses specific computing rules or instructions to predict or generate a response to a query, e.g., clinical trial questions, provided by a user. In particular, the computing system utilizes a model that contains a natural language processor (NLP) module and a Machine Reasoning as a Service (MRaaS) module to generate the response. The NLP module can recognize or identify the contextual meanings of each of the words or phrases in the query. The MRaaS module can generate the response using the contextual meanings of each of the words from the query provided by the NLP module.

The MRaaS module can rely on an artificial intelligence (AI) system that employs ontologies, knowledge graphs, reasoning through use of an inference engine and an explainability module, and clinical trial data provided by external sources, e.g., clinical trial expert knowledge. The MRaaS can provide a response with a high confidence level. More specifically, the MRaaS module can generate and provide reasoning and identified sources behind the response to the user using the inference engine and the explainability module. The computing system can capture interactions from the user responding to the identified reasoning, and provide feedback and various other types of recommendations to improve the model's accuracy.

In some implementations, the computing system utilizes the MRaaS module and an NLP module to derive a response to the query. The MRaaS module can process terms from the query provided by the NLP module that recognizes and extract terms from the query. The MRaaS module can semantically understand relevant terms, e.g., medical and clinical terms, their relations to other medical terms. Additionally, the NLP module can extract terms from external information or sources, such as textbooks, online resources, and medical journals or from unstructured datasets such as electronic medical data for multiple healthcare patients. In some implementations, the NLP module can include one or more machine learning algorithms. The NLP module can be trained using the one or more machine learning algorithms, e.g., deep learning algorithms. In some cases, the NLP module can be external to the computing system.

The NLP module can provide the extracted terms and their contextual meanings to the MRaaS module. In some implementations, the MRaaS module can identify a set of ontologies based on a domain of a specific subject and associated with the specific user that provided the response. The MRaaS module can use characteristics associated with the user to identify the set of ontologies, such as user identification, job type, and user location, to name a few examples. In response to identifying the set of ontologies, the MRaaS module can select a subset of ontologies from the set of ontologies based the extracted terms and their contextual meanings identified by the NLP module. The MRaaS module can then identify one or more knowledge graphs based on the selected subset of ontologies. If the MRaaS module identifies that one or more knowledge graphs are not returned, the MRaaS module can generate the one or more knowledge graphs based on the selected subset of ontologies.

In some implementations, the MRaaS module traverses the one or more knowledge graphs to identify a response. For example, the MRaaS module can traverse a path over multiple nodes in the one or more knowledge graphs that match to the extracted terms and contextual meanings of those terms provided by the NLP module. The end nodes of the path can correspond to the responses to the query provided by the user. Additionally, the MRaaS module can track the path traversed from start to finish in the one or more knowledge graphs. In response, the MRaaS module can generate a response to the query that includes the data identified at the end nodes of the path. The data may include, for example, structured medical documents, results of previous clinical trials, answers to medical questions, or other types of medical information. The MRaaS module can transmit the generated response to the client device of the user. Additionally, the MRaaS module can transmit data illustrating the path traversed from start to finish in the one or more knowledge graphs illustrating how the MRaaS module derived at its answer. By providing both the generated response and the traversed path, a user can analyze results of the generated response and visualize how the computing system arrived at the results.

In some implementations, the user can provide feedback to the computing system based on the generated results and the derivation of the computing system's response. For example, if the user does not agree with the results or determines that the computing system missed important features when deriving the response, the user can provide feedback to the computing system with the corrections. The computing system can update its processes, generate a new response with data identifying how the new response was derived, and provide this information to the user. In this manner, one benefit of this system includes this feedback loop, in which the computing system can continuously improve predicting or generating responses to queries over time. By providing the derived reasoning for each generated response and receiving feedback to update the derived reasoning, the computing system can over time move closer to ideal responses for user queries.

In one general aspect, a method performed by one or more computers includes: obtaining, by the one or more computers, a query from a client device associated with a user, the query comprising a plurality of terms; determining, by the one or more computers, a meaning for each term or group of terms in the plurality of terms; determining, by the one or more computers, user data for the user that submitted the query; identifying, by the one or more computers, one or more ontologies based on the meanings for at least some of the terms in the plurality of terms; identifying, by the one or more computers, a knowledge graph based on the one or more identified ontologies and the user data; generating, by the one or more computers, a response to the query by traversing a particular path of the identified knowledge graph to identify one or more items in the knowledge graph based on the determined meaning for each of the terms or group of terms; generating, by the one or more computers, path data that represents the particular path taken by the one or more computers through the identified knowledge graph; and providing, by the one or more computers, the generated response that comprises the one or more identified items and the path data to the client device for output.

Other embodiments of this and other aspects of the disclosure include corresponding systems, apparatus, and computer programs, configured to perform the actions of the methods, encoded on computer storage devices. A system of one or more computers can be so configured by virtue of software, firmware, hardware, or a combination of them installed on the system that in operation cause the system to perform the actions. One or more computer programs can be so configured by virtue having instructions that, when executed by data processing apparatus, cause the apparatus to perform the actions.

The foregoing and other embodiments can each optionally include one or more of the following features, alone or in combination. For example, one embodiment includes all the following features in combination.

In some implementations, the method includes wherein the determined user data comprises one or more of a location of the user or a job position of the user.

In some implementations, the method includes wherein determining the meaning for each term in the plurality of terms further comprises: parsing, by the one or more computers, the plurality of terms into separate terms; and identifying, by the one or more computers, entities and relationships from each of the separate terms, wherein the entities correspond to clinical terms and the relationships correspond to clinical actions performed by or for the entities.

In some implementations, the method includes wherein identifying the one or more ontologies based on at least some of the meanings for each of the terms in the plurality of terms comprises: storing, by the one or more computers, a plurality of ontologies in an ontology Knowledge base, each ontology in the plurality of ontologies built using historical medical data that comprises at least one of previous clinical trial data, clinical journals, biology data, life sciences data, genetic data, disease data, and pharmacological data, and the historical medical data is stored in each of the ontologies in a structured manner; retrieving, by the one or more computers, one or more ontologies based on the user data; and selecting, by the one or more computers, a subset of ontologies from the one or more retrieved ontologies based on a match between historical data in the subset of ontologies to at some of the meanings for each of the terms in the plurality of terms.

In some implementations, the method includes wherein identifying the knowledge graph based on the one or more identified ontologies and the user data further comprises: identifying, by one or more computers, the knowledge graph from a plurality of stored knowledge graphs, each stored knowledge graph of the plurality of stored knowledge graphs connecting entities and corresponding relationships; wherein identifying the knowledge graph from the plurality of stored knowledge graphs further comprises: identifying, by the one or more computers, the knowledge graph that matches to the subset of the ontologies; and providing, by the one or more computers, the identified knowledge graph to an inference engine for determining the path data.

In some implementations, the method includes wherein generating the response to the query by traversing the particular path of the identified knowledge graph to identify one or more items based on the determined meaning for each term further comprises generating, by the one or more computers, the response to the query from the client device by (i) traversing the particular path of the identified knowledge graph based on the determined meaning for each term and (ii) accessing the one or more items located at an end of the particular path.

In some implementations, the method includes wherein generating the path data that represents the particular path taken by the one or more computers through the identified knowledge graph further comprises tracking, by the one or more computers, the particular path taken by the one or more computers through the identified knowledge graph that comprises matching the meaning for each term in the plurality of terms to entities and relationships in the identified knowledge graph.

In some implementations, the method includes wherein providing (i) the generated response to the query and (i) the particular path tracked and taken by the one or more computers through the identified knowledge graph to the client device further comprises transmitting, by the one or more computers, the response to the client device over a network.

In some implementations, the method includes in response to providing the generated response to the query to the client device for output, receiving, by the one or more computers, an update from the client device that comprises one or more modifications to the one or more identified ontologies and to the identified knowledge graph; and modifying, by the one or more computers, the one or more identified ontologies or the identified knowledge graph based on the update that comprises the one or more modifications.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

FIG. 2C is a block diagram that illustrates an example of a system for traversing a knowledge graph within the MRaaS module.

Like reference numbers and designations in the various drawings indicate like elements. The components shown here, their connections and relationships, and their functions, are meant to be examples only, and are not meant to limit the implementations described and/or claimed in this document.

DETAILED DESCRIPTION

Current search systems can store and access medical information in an unstructured data format and the medical information may be dispersed across a vast number of systems, which makes it difficult for information to be linked and ultimately, queried by external users. Many sources of this medical information are text-based sources and the information can be formed from a variety of elements. However, there is no international or existing categorization of these different elements that is widely followed.

When querying information from these medical sources, domain expertise is often required to recognize relevant terms, categorize the terms based on meaning, and convert the terms to a suitable format that can be then used for data querying. The ability to model and structure this medical information enables users to derive certain insights that can improve health conditions, improve medical clinical trial practices, and assisting with postulating new medical theories, to name a few examples. Additionally, if responses to queries result in inaccuracies or do not specifically respond to the query, users may perform additional tasks based on misleading information, causing inefficiencies and potentially detrimental health effects to patients. To address these inaccuracies, a system is needed that can provide responses to complex medical queries and identifies how the responses were generated.

In this context, techniques are described in this specification for generating a predictive model that recognizes clinical terms and a relationship between the terms, and provides a response to the query using a Machine Reasoning as a Service (MRaaS) module. In particular, a computing system can receive a query from a user or other structured and unstructured datasets, e.g., external medical databases, medical journals, textbooks, and other data sources, using a natural language processor (NLP) module and other deep learning algorithms. The techniques use the NLP module to recognize, extract, and categorize medical entities, e.g., indications, drugs, diseases, procedures, etc., as well as determine relationships between the medical entities with reference to the terms that describe the entities.

The information extracted from the NLP module is provided to the MRaaS module for querying and providing a response to the query. In particular, the MRaaS module can derive a response using various ontologies, knowledge graphs, and other historical medical data. Typically, the queries provided to the computing system are focused on complex medical terms that are relevant to a clinical study, a clinical procedure, or clinical research to name a few examples. The MRaaS module can provide a response to the query as well as data identifying how the MRaaS module derived at the response.

Figure 1A:
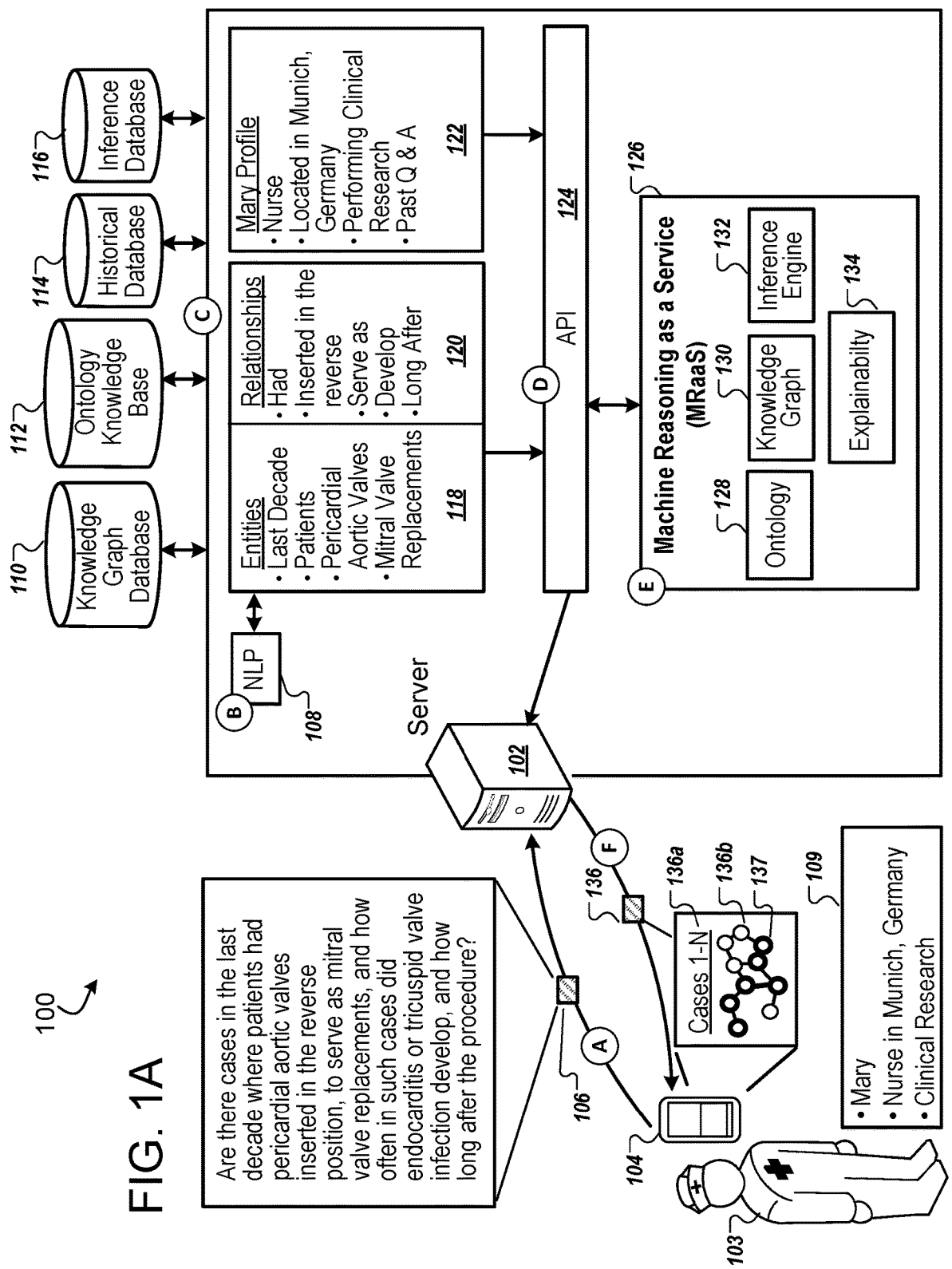
FIG. 1A is a block diagram that illustrates an example of a system for generating a response to a query using Machine Reasoning as a Service (MRaaS).

FIG. 1A is a block diagram that illustrates an example of a system 100 for generating a response to a query using the MRaaS module. System 100 can be a predictive computing system configured to process input data to train a predictive model. The predictive model can be trained to generate an accurate response provided by a user and to provide data that identifies how the response was generated. In general, system 100 can receive a query from medical personnel, such as a nurse, clinician, doctor, or other, and can provide clinically relevant responses to the query. FIG. 1A illustrates various operations in stages (A) though (F) which may be performed in the sequence indicated or another sequence.

In some implementations, system 100 includes a client device 104, a server 102, a knowledge graph database 110, an ontology knowledge base 112, a historical database 114, and an inference database 116. The server 102 can include one or more computers connected locally or connected over a network. The one or more computers of the server 102 can include an NLP module 108, one or more application programmable interfaces (APIs) 124, and an MRaaS module 126. The server 102 is configured to communicate with the client device 104 over a network. The network can include for example, a local network, such as Bluetooth or Wi-Fi, or a larger network, such as the Internet. Alternatively, a user may directly interact with the server 102 by way of a touchscreen, or a monitor, keyboard, and mouse.

The server 102 may include one or more computers connected locally or over a network. The server 102 may also communicate with the knowledge graph database 110, the ontology knowledge base 112, the historical database 114, and the inference database 116. The server 102 can communicate with the client device 104 to obtain a query, provide results of the query, obtain feedback from the results, and provide new results of from the feedback, for example. The server 102 can also communicate with the client device 104 for other purposes, such as authorization and login purposes. The server 102 can communicate with the databases or data stores 110, 112, 114, and 116 to obtain medical, ontology, knowledge systems, and other information for generating the response to the query.

During stage (A), a user 103 provides a query 106 to the server 102. The user 103 may correspond to a medical clinician, e.g., doctor, medical researcher, nurse, or other, which seeks an answer to a particular question. For example, the user 103 may be researching a complex medical topic and provide a query that recites "Are there cases in the last decade where patients had pericardial aortic valves inserted in the reverse position, to serve as mitral valve replacements, and how often in such cases did endocarditis or tricuspid valve infection develop, and how long after the procedure? The user 103 can interact with the client device 104 to enter the query 106 via typing, speaking, or interacting with a touchscreen of the client device 104.

In some implementations, the client device 104 transmits additional information to the server 102 in the query 106. The additional information can include information about the user, such as credentials of the user 103 for authorization to communicate with server 102, e.g., username and password, data identifying the client device 104, and a location of the client device 104, e.g., locational coordinates. The additional information can also include a job position of the user 103, e.g., the user's job title, a characterization of the user's job responsibilities, a job title at the particular location, or a job category. For example, the job position may correspond to a nurse, a researcher, a doctor, a secretary, or some other position. The user's job position may change depending on the user's location. As illustrated in system 100, data 109 illustrates corresponding information about user 103. User 103's name is Mary, she is currently located in Munich, Germany, and her role for this query corresponds to clinical researcher.

The client device 104, which can include a personal handheld device, a mobile device, a tablet, a personal computer, or other, receives the user 103's input and transmits the query 106 to the server 102. The client device 104 transmits the query 106 over a network. Alternatively, if the client device 104 is connected to the server 102, e.g., a display for user interaction connected to the server 102, and then the server 102 can accept the query 106 in response to the user 103's entry.

During stage (B), the server 102 receives the query 106 from the client device 104. In some implementations, the server 102 can recognize and determine that the query 106 corresponds to a request from a particular user, e.g., user 103. For example, the server 102 can first authorize the user's access to respond to the query 106 by comparing stored credentials to credentials provided in the query 106. If the server 102 determines that a match does not exist, the server 102 denies user 103's access to perform the search. Alternatively, if the server 102 determines that a match does exist, the server 102 can identify the user that transmitted the request 106 as the user 103, e.g., Mary.

In some implementations, the server 102 includes the NLP module 108 that is used to obtain the query 106 and process the query 106. In particular, the NLP module 108 can include one or more high-level programming languages that are programmed to recognize and extract a plurality of terms from the query 106. For example, the NLP module 108 can include a python or a java module that uses coded instructions to identify terms and words that describe medical entities for different medical entities in the query 106. In some cases, the NLP module 108 can include one or more trained machine learning algorithms to identify terms and words from the received query. The NLP module 108 can receive the query 106 and can parse the query into one or more words. For example, the NLP module 108 can parse the query 106 to identify these words: "Are," "there," "cases," . . . "how," "long," "after," "the," and "procedure", among others.

In some implementations, the NLP module 108 can generate entities 118 from the parsed query 106 and relationships 120 from the parsed query 106. For example, each word or term identified in the query 106 can be searched against a data source, such as a dictionary of specific medical terms or a textbook that describes medical concepts. Based on the definition or description of each word in the query 106, the NLP module 108 can separate the words from the query 106 into entities 118 and relationships 120. The server 102 can define entities as medical entities, such as nouns, e.g., indications, drugs, procedures, time periods, medical parts, clinical terms etc., and the relationships defined as the relationships between the identified medical entities with reference to the terms that describe the entities, such as actions performed by or for the entities.

As illustrated in system 100, the server 102 can define entities 118 to include the following: "last decade", "patients", "pericardial aortic valves", and "mitral valve replacements". The entities 118 may include more or less words from the query 106 than those illustrated in system 100. Likewise, the server 102 can define the relationships 120 to include the following: "had", "inserted in the reverse", "serve as", "develop", and "long after". In addition, the relationships 120 may include more or less words from the query 106 than those illustrated in system 100.

The server 102 can identify a location of the user 103. For example, the server 102 can identify from the locational coordinates provided in the query 106 by the client device 104 that the user 103 is currently located at a place in Munich, Germany. Additionally, the server 102 can identify a job location of user 103. For example, the server 102 can identify that user 103 works in Munich, Germany but is currently located in London, based on locational coordinates from the client device 104, such as for vacation. In this case, the server 102 can identify a job location of user 103 by identifying a job location of a user profile associated with user 103. The user profile can indicate the job location for user 103, e.g., Munich, Germany. In this example, the server 102 can identify the relevant location of the user 103 as Munich, Germany, even though the user is currently located in London.

In some implementations, the server 102 can prompt the client device 104 with an identified location and request the user 103 to indicate the relevant location. For example, the server 102 can indicate to the client device 104 that the user 103 has been identified in a particular location, e.g., London, UK, but that the server 102 identifies the user 103's relevant job location to be Munich, Germany. The client device 104 can ask the user 103 if the relevant location should be Munich, Germany, e.g., the identified job location, or London, UK, e.g., the user 103'3 current location. The user 103 can select one of these locations to aid the server 102 in identifying one or more ontologies. In other implementations, the server 102 can automatically select the relevant job location of user 103 no matter where the user 103 is located. Alternatively, the server 102 can select the current location of user 103 as the relevant location for ontology selection.

The server 102 can also identify another characteristic of user 103 that indicates a current job position of user 103. In some implementations, the server 102 can determine from the query 106 the current job position of user 103. For example, the query 106 can indicate that the user 103 is performing clinical research, as indicated in data 105. In some implementations, the server 102 may track job positions of user 103. If the query 106 did not include a job position of user 103, then the server 102 can access in memory or in a database previously performed jobs for user 103. These previously performed jobs can for user 103 can include nurse, performing clinical trials, assistant in surgery, or another job type.

In some implementations, the server 102 builds a profile 122 of the user 103 based on the determined characteristics. For example, the server can generate the profile 122 to include an identification of Mary, e.g., user 103, as a nurse and that Mary is located in Munich, Germany. Additionally, the generated profile 122 can include an indication that Mary is sending in the query 106 to perform clinical research.

During stage (C), the server 102 accesses and retrieves data from the knowledge graph database 110, the ontology knowledge base 112, the historical database 114, and the inference database 116. The server 102 can access each of these data stores, e.g., databases, warehouses, data links, and others, for providing additional information to the MRaaS module 126. The server 102 can access these data stores using the determined characteristics of the user 103, such as the characteristics identified in the profile 122.

In some implementations, the ontology knowledge base 112 includes one or more ontology knowledge databases that store a variety of ontologies. An ontology corresponds to a data structure that stores and shows the properties of a subject matter and how these properties are interrelated, by defining a set of concepts and categories that represent the subject area.

For example, one example of such an ontology corresponds to the medical dictionary for regulatory activities terminology (MEDDRA). MEDDRA is an international medical terminology with an emphasis on use for data entry, retrieval, analysis and display. MEDDRA is an ontology that can apply to all phases of drug development, excluding animal toxicology, and to the health effects and malfunction medical devices. In some examples, the ontology knowledge base 112 includes other ontologies such as Alzheimer's disease ontology, antibiotic resistance ontology, asthma ontology, gene ontology, disease ontology, pharmacological ontologies, bioscience ontology, and others. The ontology knowledge base 112 can include any appropriate ontology, such as any medical ontology that can be accessed from other medical departments and ontologies found on the Internet.

In some implementations, the server 102 retrieves one or more ontologies from the ontologies knowledge base 112 based on one or more of the determined characteristics of user 103. In particular, the server 102 may store a relationship between the determined characteristics of user 103, e.g., an identification of user 103, a location of user 103, e.g., more specifically a location of client device 104 of user 103, and a current job position of user 103. For example, the server 102 may store a relationship or an index to an ontology when user 103 is located in Germany. The index may include a tag that describes user 103 being located in Germany and corresponds to MEDDRA ontology, antibiotic resistance ontology, heart ontology, asthma ontology, and disease ontology, to name a few examples. Other examples are also possible. The server 102 retrieves one or more ontologies from the ontologies knowledge base 112 based on the determined characteristics of the user 103 because the server 102 expects certain ontologies to be applicable to the user 103's queries and desired responses. Certain ontologies may be relevant to a certain user when the user is located in a particular location and other ontologies may be more relevant to that user when that user is location in another location.

In this example, when the server 102 determines that user 103 is located in Germany or the relevant location of the user when the user is located in another location, the server 102 can retrieve the MEDDRA ontology, antibiotic resistance ontology, heart ontology, asthma ontology, and disease ontology. Additionally, when the server 102 determines that the user is user 103, the server 102 can retrieve various ontologies from the ontology knowledge database 112 that is indexed by an identification of user 103. For example, when the server 102 determines that the user is user 103, the server 102 can retrieve the biology ontology, genetics ontology, biofilm ontology, and the biomedical ontology models. In another example, the server 102 can retrieve various ontologies for when user 103 performing a particular job, e.g., a nurse or a clinical researcher, for example. Some of these ontologies may overlap with one another between different characteristics of the user 103. The reason the locations, users, and job types are associated with different ontologies is because the user 103 may perform different types of work at these locations.

In some implementations, the server 102 can obtain ontologies for more than one determined characteristic of the user 103. The ontologies can be associated with two or more characteristics of user 103. For example, if the server 102 determines that the user 103 is Mary and is located in Munich, Germany, then the server 102 can filter and retrieve ontologies that are associated or indexed by these two determined characteristics. Other combinations are also possible. Additionally, the server 102 can identify and retrieve ontologies that are associated or indexed by three determined characteristics in a similar manner as described above. In some implementations, the user 103 may indicate to the server 102 which ontologies to use for the query and provide descriptions of the ontologies in the query 106. In some implementations, the server 102 can obtain ontologies using the determined characteristics of the user 103 and some of the terms identified from the provided query 106.

In some implementations, the historical database 114 can store profiles for various users that access the server 102. Each profile can include characteristics about the corresponding user, such as various jobs held, various locations worked, and identifications of the users, e.g., credentials and names. When a user transmits a query 106 to the server 102, the server 102 can access a corresponding profile from the historical database 114 and compare the contents of a stored profile to determined characteristics of the user associated with the query 106. If a difference exists, then the server 102 updates the corresponding profile(s) for that user in the historical database 114.

Additionally, the explainability module 134 can determine how the MRaaS module 126 arrived at its conclusion or response based on previous determinations. The explainability module 134 can rely on backward chaining functions from logical inference to generate path data that explains how the MRaaS module 126 arrived at its conclusion or response. This will be further described below.

In some implementations, the knowledge graph database 110 includes one or more databases that store a repository of knowledge graphs in relation to the user. A knowledge graph, also known as a sematic network, can represent a network of real-world events, e.g., objects, events, situations, or concepts, and can illustrate the relationship between these events. A knowledge graph is typically visualized as a graphical structure and includes various components. For example, a knowledge graph is typically created of three main components—nodes, edges, and, labels. A node can correspond to an object, a place, or a person. An edge can correspond to a relationship between one or more nodes. A label can correspond to the description that defines the relationship between one or more nodes.

In the context of system 100, an example of a knowledge graph may correspond to a medical condition, such as heart disease. The nodes may correspond to different types of heart disease. The edges can correspond how to these different heart diseases can relate, such as through symptoms of the different types of heart disease. The labels can describe the nodes and the relationships between the nodes.

In some implementations, each knowledge graph corresponds to one or more ontologies stored in the ontology knowledge database 112. Generally, a knowledge graph can visually illustrate the data extracted from one or more ontologies. The ontologies can store this data in a formal and structured manner. Alternatively, the data identified in multiple knowledge graphs may be stored across multiple ontologies. The knowledge graph can be associated to a user or a user profile, such as profile 122.

In some implementations, the historical database 114 includes one or more databases that store previously generated and accessed data for generating the response to the query. Generally, the historical database 114 stores previous queries, previous generated responses associated with the previous queries, previously determined entities and relationships associated with the previous queries, and other previously generated data. This can include corresponding ontologies, knowledge graphs, inference engines, previously generated explainability models, and paths produced by the previously generated explainability models, each of these associated with a previously received query and a generated response, to name a few examples.

For example, the historical database 114 can store a timestamped log that illustrates each of the data components used by the server 102 to generate the response for a received query. The log can be indexed by the query received and store data generated and utilized by the server 102 to generate the response. In this manner, a supervisor or designer of system 100 may be able to review the log to monitor the performance and adjustments made by the server 102 for each query.

In some implementations, the historical database 114 can provide the server 102 access to external medical documents. The external medical documents can correspond to structured and unstructured data. The structured data can include various types of medical publications and health-related text, such as medical textbooks, online publications relating to healthcare, medical journals, electronic publications, medical treatises, web-based articles, medical websites, or various resources of information that can be formatted for data extraction and processing by a computer system, e.g., the server 102. The unstructured data may correspond to different datasets that relate to medical activities, patient medical records, or healthcare transactions. Additionally, the historical database 114 can provide the server access to websites and other cloud storage components that enable the server 102 to search for various medical data, e.g., medical journals, texts, and other peer-reviewed documents.

In some implementations, the inference database 116 can store results from the inference engine. The inference database can save the results from the inference engine and provide the results back to the user and results provided to the ontologies and knowledge graphs for future reasoning in response to queries. Inference can correspond to the process of deriving new sentences from old sentences or deriving implicit knowledge from explicit knowledge. An inference algorithm, executed by the inference engine, can derive only entailed sentences, which is known as sound or truth preserving. Soundness from an inference algorithm is a highly desirable property. An unsound inference algorithm can essentially generate inferences as it continuously processes. Sound inference algorithms derive only sentences that are entailed. For example, sound inference algorithms operates by storing sentences about that the world in the knowledge and ontology databases, using the inference mechanism to infer new sentences, and using these sentences to describe what action to take. As such, the inference engine is a rules-based built module from logic and uses logical reasoning to derive assertions or rules.

During stage (D), the server 102 communicates through an application programmable interface (API) 124 to provide data associated with the query 106 to the MRaaS module 126. The API 124 corresponds to a source code interface that enables a system, such as server 102, to access functions and other items from a software application. The API 124 can be specified in terms of a programming language, e.g., python, C++, C, Java, Ruby, etc., that can be interpretative or compiled when an application, e.g., MRaaS module 126, is built. The software that provides the functionality described by the API 124 can be an implementation of the API 124.

In some implementations, the server 102 can provide data associated with the query 106 to the MRaaS module 126 through the API 124. Generally, the API 124 may use a variety of inputs for the MRaaS module 126 to determine a response to the query 106. For example, the server 102 can provide data representing the entities 118, the relationships 120, the profile 122, one or more retrieved knowledge graphs from the knowledge graph database 110, one or more retrieve ontologies from the ontology knowledge database 112, previous data and external medical documents from the historical database 114, and previously determined inferences from the inference database 116. In some implementations, the server 102 may only provide a subset of the aforementioned data.

The data representing each of the inputs to the API 124 may be provided in various formats. For example, the server 102 can provide the data as pointers, linked-lists, a link to a location in memory or in a database, or the data for each of the inputs itself. In response to the server 102 providing the inputs via the API 124 to the MRaaS module 126, the MRaaS module 126 can perform the process of generating a response to the query 106.

During stage (E), the server 102 executes the functions of the MRaaS module 126. The MRaaS module 126 can include one or more modules, such as ontology module 128, a knowledge graph module 130, an inference engine 132, and an explainability module 134. Each of the modules 128, 130, and 134 and engine 132 can communicate with one another. Additionally, each of the modules of the MRaaS module 126 may communicate with the various databases connected to the server 102, e.g., the knowledge graph database 110, the ontology knowledge base 112, the historical database 114, and the inference database 116. In some implementations, the modules within the MRaaS module 126 may communicate with one or more external client devices, such as client device 104, over a network.

The ontologies module 128 can receive the ontologies provided through the API 124 that were identified based on the determined characteristics of the user 103. The server 102 identified ontologies from the ontology knowledge base 112 based on the determined characteristics of the user 103, e.g., an identification of user 103, a location of user 103, and a current job role of user 103. These ontologies were initially identified because the server 102 can determine that the user 103 typically works with these ontologies when at a particular location and/or when performing a current job. In this sense, these ontologies can be identified to speed up the process of identifying ontologies that match to the one or more terms and their corresponding meaning as provided in the query 106.

For instance, the ontology module 128 can search through the already provided ontologies to identify the subset of ontologies based on the one or terms and their corresponding meaning as provided in the query 106. If this initial identification process were not taken, the ontology module 128 would be searched through each of the ontologies in the ontology knowledge base 112, which wastes resources, processing power, and time. Therefore, the ontology module 128 can search over a smaller set of ontologies to identify the correct subset of ontologies.

In this case, the ontology module 128 may receive the following ontologies associated and based on the determined characteristics of the user 103: the MEDDRA ontology, Alzheimer's disease ontology, antibiotic resistance ontology, heart disease ontology, asthma ontology, gene ontology, disease ontology, pharmacological ontologies, and bioscience ontology, for example. Then, the ontology module 128 can identify a subset of ontologies from the received ontologies based on the terms indicated in the entities 118, the relationships 120, and the profile 122. The ontology module 128 can perform, for example, string matching, partial matching, and other matching functions, with the entities 118, the relationships 120, and the profile 122 to determine a confidence level that indicates a likelihood that the corresponding ontology is relevant to the query. For example, the words identified in the entities 118 and the relationships 120 may match to the structured data included in a particular ontology. The more words that match between the entities 118, the relationships 120, and the profile 122 to the particular ontology, the higher likelihood that a particular ontology is relevant to the query 106.

In some implementations, the ontology module 128 may weigh factors more heavily than others when retrieving ontologies using the values provided by the NLP module 108. The words in the entities 118 may carry a higher weight than the words included within the relationships 120. For example, the ontology module 128 may weight the words in the entities 118 to 65% whereas the words in the relationships 120 may be weighted with a value of 20%. Thus, a match between data included in the identified ontology and a word from the entities 118 will carry a higher weight than a match between data included in the identified ontology and a word from the relationships 120. Other examples of assigning weight values to different inputs are also possible. Generally, the ontology module 128 can generate a confidence level for an ontology according to the weights assigned to the values produced by the NLP module 108 to ensure any identified ontologies more closely resemble the query 106. The confidence level can be, for example, a percentage that ranges from zero to 100, or a number ranging from zero to one.

In some implementations, in response to generating a confidence level for a particular ontology, the ontology module 128 can discard any ontologies that fall below a particular threshold. For example, if the ontology module 128 sets a threshold level of 75% and the ontology module 128 determines an Alzheimer's ontology matches to the entities 118, the relationships 120, and the profile 122 with a generated confidence level of 60%, then the ontology module 128 can discard the Alzheimer's ontology. On the other hand, if the ontology module 128 determines a heart disease ontology matches to the entities 118, the relationships 120, and the profile 122 with a generated confidence level of 90%, then the ontology module 128 can keep and save the heart disease ontology. The ontology module 128 can iterate through each of the provided ontologies through the API 124.

If the ontology module 128 determines that none of the provided ontologies has a confidence level greater than the threshold level, the ontology module 128 can transmit a notification back to the API 124 to indicate that additional ontology models are requested from the ontology knowledge base 112. In some implementations, the ontology module 128 may directly retrieve ontologies from the ontology knowledge-base 112 based on one or more of the determined characteristics of the user 103 to try to identify ontologies that match the query 106. If a match does not exist, the MRaaS module 126 can transmit a notification to the client device 104 indicating an error has occurred and asking for additional guidance on which ontologies to identify. In some implementations, the MRaaS module 126 may not provide indications of which ontologies are available. In this case, the MRaaS module 126 can determine which knowledge graphs and ontologies are available and can provide results from the available knowledge graphs and ontologies.

In response to the ontology module 128 identifying the ontologies that match to the contents of the query, e.g., entities 118, relationships 120, and profile 122, the ontology module can transmit the identified ontologies to the knowledge graph module 130. For example, from the ontologies received by the ontology module 128, e.g., MEDDRA ontology, Alzheimer's disease ontology, antibiotic resistance ontology, heart disease ontology, asthma ontology, gene ontology, disease ontology, pharmacological ontologies, and bioscience ontology, the ontology module 128 can select a subset of those ontologies based on their confidence levels: MEDDRA ontology, antibiotic resistance ontology, heart disease ontology, gene ontology, disease ontology, and pharmacological ontology.

In some implementations, the knowledge graph module 130 can receive the identified ontologies and identify one or more knowledge graphs that match to the identified ontologies. As previously described, a knowledge graph can typically correspond to a graphical structure, such as a semantic network, that illustrates a network of nodes and the relationships between the nodes in the network of nodes. In order to generate the semantic network of the knowledge graph, a knowledge graph can use one or more data sources to create its network. In particular, the data sources for the graphs correspond to one or more ontologies. In the case of system 100, the knowledge graph module 130 can identify one or more knowledge graphs that were provided by the ontology module 128.

In some implementations, the knowledge graph module 130 can determine whether one or more knowledge graphs were previously generated or instantiated from the identified ontologies provided by the ontology module 128. The knowledge graph module 130 can analyze previously generated or instantiated knowledge graphs by reviewing data properties that are stored in memory in the server 102 or the ontology knowledge base 112. The data properties can describe the nodes, the relationships between the nodes, the labels that describe the relationships between the nodes. The server 102 can monitor, track, and store the data properties each time a new knowledge graph is created or when a knowledge graph is modified based on edits made to the one or more ontologies that supports the underlying architecture of the knowledge graph.

The knowledge graph module 130 may identify whether the received ontologies match to any previously generated knowledge graph. The knowledge graph module 130 may determine that a previously generated knowledge graph was created from one or more of the received ontologies. If the knowledge graph module 130 determines that one of the previously generated knowledge graphs was instantiated from at least one of the received ontologies, then the knowledge graph module 130 can edit that knowledge graph by incorporating the data structures from the other received ontologies. For example, the knowledge graph module 130 may determine that knowledge graph A was instantiated from a skin disease ontology, an asthma ontology, and a MEDDRA ontology. In this example, the knowledge graph module 130 can receive the following ontologies: MEDDRA ontology, antibiotic resistance ontology, heart disease ontology, gene ontology, disease ontology, and pharmacological ontology. In response, the knowledge graph module 130 can determine that knowledge graph A was instantiated from an ontology that was also received from the ontology module 128, e.g., the MEDDRA ontology. In this example, the knowledge graph module 130 can modify knowledge graph A to incorporate the data from the other ontologies, e.g., antibiotic resistance ontology, heart disease ontology, gene ontology, disease ontology, and pharmacological ontology.

In some implementations, if the knowledge graph module 130 determines no stored knowledge graphs were instantiated with ontologies that match to the received ontologies, then the knowledge graph module 130 can generate a new knowledge graph. The knowledge graph module 130 can generate a new knowledge graph based on the received ontologies, e.g., MEDDRA ontology, antibiotic resistance ontology, heart disease ontology, gene ontology, disease ontology, and pharmacological ontology. Alternatively, if the knowledge graph module 130 determines that a stored knowledge graph was instantiated with ontologies that each match to the received ontologies, then the knowledge graph module 130 can retrieve the stored knowledge graph for usage.

In response to identifying a knowledge graph, the knowledge graph module 130 can transmit data representing the knowledge graphs to the inference engine 132. In some implementations, the inference engine 132 can process the data in the received knowledge graph and generate results for the query. The inference engine 132 can also receive a previously generated inference engine from the inference database 117 for processing the data in the received knowledge graph. Additionally, the inference engine 132 can receive data from the query including the query 106, the entities 118, the relationships 120, and the profile 122. Additionally, the inference engine 132 can receive the corresponding one or more ontologies from the ontology module 128 that corresponds to the received knowledge graph from the knowledge graph module 130. The inference engine 132 can utilize all the received data to produce one or more entities in response to the provided query. The inference engine 132 can receive this data in the form of the data itself, a struct, a pointer to a location in memory, or a pointer to a location in external memory, e.g., a database, to name a few examples.

In some implementations, the inference engine 132 can traverse, search, or review a knowledge graph to induce or determine a particular conclusion. The conclusion can correspond to the MRaaS module 126's results or response to the query 106. Generally, the inference engine 132 traverses the knowledge graph to determine the conclusion based on the group of terms and their corresponding meaning from the query 106. For example, in the medical domain, the inference engine 132 can determine or identify several cases that illustrate infections that developed after a particular medical procedure, such as a heart procedure. The inference engine 132 can search the knowledge graph for entities describing these types of cases, in this example. The knowledge graph can applicable to other cases, such as heart disease domain, disease domain, or other domains represented by the corresponding ontologies.

The inference engine 132 can scan or traverse a knowledge graph to identify these entities based on one or more criteria. For example, the inference engine 132 can hop from one node to another node along an edge that connects the two nodes when the data representing these corresponding components match to the entities 118, relationships 120, and profile 122 to a particular degree. The inference engine 132 may determine that the entities and relationships represented by the nodes and edges in the knowledge graph, respectively, match to the entities 118 and relationship 120 based on statistics, probabilities, or other factors.

In some implementations, the inference engine 132 may determine which path take between multiple nodes based on previous path selections for other requests. The inference engine 132 may take previous decisions for other requests into consideration as the inference engine 132 determines the traversed path in the knowledge graph. In order for the inference engine 132 to make a determination based on previous path selections, the inference engine 132 can enable knowledge graphs to communicate with one another. For example, the knowledge graph database 110 may store a knowledge graph that tracks path connections from previous path traversals. For example, the knowledge graph may correspond to a historical knowledge graph that tracks different users usages, queries asked, results determined from the queries, and previous node connections for the queries asked. In other example, the knowledge graph database 110 can store multiple knowledge graphs that share knowledge and link together to form larger knowledge graphs. The knowledge graph database 110 can store data describing the links between multiple knowledge graphs.

For example, in a medical domain, the inference engine 132 may determine that in a knowledge graph, a node A corresponds to "Mitral Valve Replacements", a node B corresponds to "Procedures", and node C corresponds to "Inversion Insertion." Moreover, the inference engine 132 can determine that node A connects to node B along an edge represented by "heart procedure" and node A connects to node C along an edge represented by "Mitral Valve." The inference engine 132 can determine that node A's "Mitral Valve Replacements" matches to a word in the entities 118, node B's "Procedure" matches to a word in the entities 118, and node C's "Inversion Insertion" matches to a word in the entities 118. However, the inference engine 132 may also determine that the edge between node A and node B that describes "heart procedure" matches to a word in the relationships 120, but the edge between node A and node C that describes "Mitral Valve" does not match to a word in the relationships 120. Thus, the inference engine 132 can decide to traverse down the edge between node A and node B based on the match. The inference engine 132 can repeat this process for identifying nodes connected to node B for traversal.

In some implementations, the inference engine 132 can repeat this process of traversing nodes in the knowledge graph until one or more nodes are reached with no further connecting edges. In response to reaching one or more nodes that have no further connecting edges, the inference engine 132 can return the values described by those nodes. In particular, the inference engine 132 can return the values or the response to the query 106 through the API 124 to the server 102. The values may be representative of the path taken by the inference engine 132 through the knowledge graph. For example, in a medical domain, the values or results can correspond to medical content, medicine to prescribe to cure illnesses, or a procedure to fix an underlying medical condition. The path taken by the inference engine 132 to reach the nodes corresponding to the returned values can represent a mapping to the contents included within the query 106. In this context, the inference engine 132 can logically identify results or responses to the query 106 by following a path in the knowledge graph that matches to contents or terms within the query 106. Ultimately, this path taken by the inference engine 132 enables the MRaaS module 126 to determine results that closely resembles or matches to the intent and content indicated by the user 103's query 106.

In some implementations, the inference engine 132 can repeat the process of traversing nodes in the knowledge graph until one or more nodes are reached that match to contents within the query 106 to a particular degree or likelihood. In particular, the inference engine 132 can identify one or more nodes and edges that match to contents from the query 106 within a location of the knowledge graph. The inference engine 132 may reach a node in the knowledge graph, for example, and identify that no further edges or nodes match to data identified in the entities 118 and relationships 120. In this case, the inference engine 132 can return the values or data represented by the identified nodes. In response to ending the traversal, the inference engine 132 can return the values or data represented by the latest node reached to the server 102 through the API 124. The values or data represented by the latest node can correspond to the results or response to the query 106. The inference can also use other methods of comparison in addition to probabilities, such as string matching or content matching.

In response to the inference engine 132 identifying one or more nodes from the knowledge graph that correspond to the results or response of the query 106, the inference engine 132 can provide data to various components within the MRaaS module 126 and data through the API 124. The inference engine 132 can transmit, for example, results of the query to the explainability module 134 and to the API 124. Similarly, the inference engine 132 can transfer data inferred from traversal of the knowledge graph to the ontology module 128. The data inferred from traversal of the knowledge graph can include the following: (i) results identified by the inference engine 132, e.g., the nodes where traversal ended; (ii) path data that indicates the path taken by the inference engine 132 through the knowledge graph; and, (iii) the statistical values illustrating the matches between the entities 118, relationships 120, and profile 122 and the data in the knowledge graph. The ontology module 128 can receive and store the inferred data associated with data from the query 106, e.g., entities 118, relationships 120, profile 122, and the data identifying the query 106 itself. In this case, the next time the server 102 receives a similar query from user 103 with these similar query parameters, the ontology module 128 can provide a similar response to the query without having to process a corresponding knowledge graph, as the results would be readily available from a previously submitted query, e.g., query 106.

In some implementations, the explainability module 134 can generate the path data that indicates the path taken by the inference engine 132 through the knowledge graph based on the received query results from the inference engine 132. For example, the explainability module 134 can generate data that illustrates a trail or path traversed through the knowledge graph of how the inference engine 132 moved from one node to the next node to identify results based on the entities 118, the relationships 120, and the profile 122 extracted from the query 106. The explainability module 134 can then provide the generated data of how the results were determined through the API 124 to be provided to the client device 104.

For example, the explainability module 134 can generate the data that illustrates a trail or path traversed through the knowledge graph in a manner that is readable and understood by a human. This data can include a visual graph showing connecting nodes and edges and a highlighted or bolded pathway through the knowledge graph from start to finish. The data can also be illustrated in bulleted, paragraphed, or some other structural documented form that describes how the inference engine 132 traversed the knowledge graph.

In some implementations, the explainability module 134 may determine from the data provided by the inference engine 132 whether to include a request for feedback in the data it plans to provide to the client device 104. The explainability module 134 can include a request for feedback to improve the overall efficiency of the MRaaS module 126.

During stage (F), the MRaaS module 126 provides the results from the inference engine 132 and the data indicating how the MRaaS module 126 determined the results from the explainability module 134 to the server 102 through the API 124. The server 102 can then provide the corresponding results and data the client device that transmitted the query.

For example, as illustrated in system 100, the server 102 can generate a data set 136 that includes the results 136a from the inference engine 132 and the data 136b from the explainability module 134. In particular, the results 136a can include the cases 1-N in answering the query 106 and the data 136b can illustrate the path traversed by the inference engine 132. The path may be, for example, bolded, highlighted, selected, or illustrated in a way to indicate to the user 103 that this was the path taken by the inference engine 132 to determine the results 136a, e.g., such as the path data 137. Additionally, the data 136b can also include feedback requested for user 103 by the explainability module 134. The feedback can be used to improve the MRaaS module 126's accuracy of processing further queries.

Figure 1B:
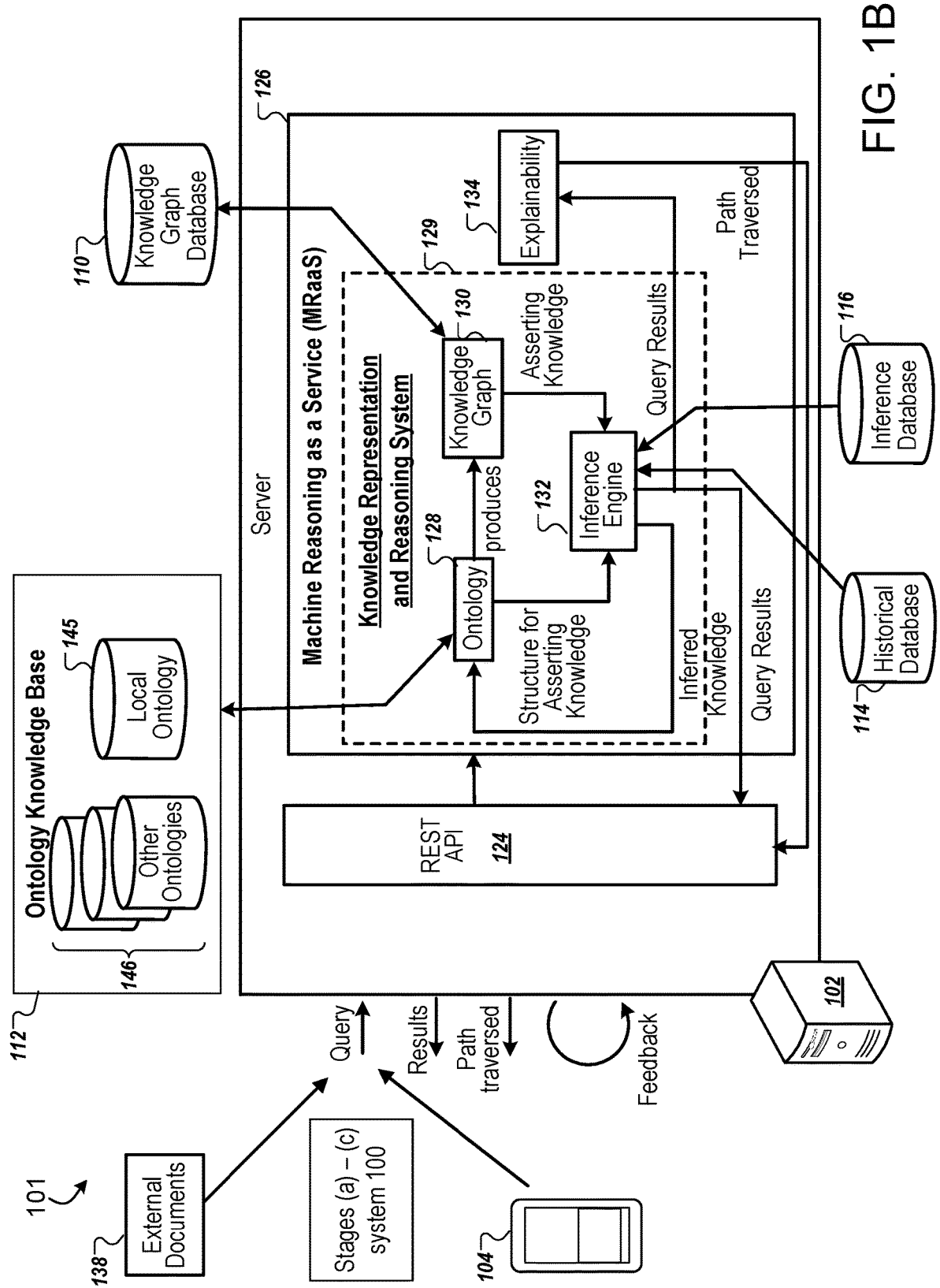
FIG. 1B is a block diagram that illustrates an example of the MRaaS module and corresponding components.

FIG. 1B is a block diagram 101 that illustrates an example of the MRaaS module 126 and corresponding components. In particular, the block diagram 101 includes similar components to the components illustrated in system 100. The block diagram 101 further includes the connections between the different components of system 100.

In the example of FIG. 1B, the server 102 can communicate with a client device 104. The client device 104 can provide a query to the server 102 and request a response with results from the query. The server 102 can obtain the query and process the query using the NLP module, similar to stages (A) through (C) performed in system 100.

The NLP module can use one or more machine learning algorithms to extract terms from the query and contextualize the terms from the query. For example, the NLP module can extract the one or more terms from the query and group the terms into entities and relationships. Additionally, the server 102 can determine one or more characteristics of the user associated with client device 104 that transmitted the query. For example, the determined characteristics can include a location of the user that interacted with the client device 104, a current job position of the corresponding user, and an identification of user. The server 102 can generate or build a profile of the user based on these determined characteristics and can store this data in the historical database 114.

In some implementations, the server 102 can then retrieve data from the knowledge graph database 110, the ontology knowledge base 112, and the inference database 117. In particular, the server 102 can retrieve a user profile from the historical database 114 and can determine whether the generated profile based on the determined characteristics of the user match the retrieved profile. If a difference exists, then the server 102 can store the differences of the user profile and the newly generated user profile in the historical database 114.

The server 102 can retrieve one or more ontologies from the ontology knowledge base 112 based on the determined characteristics of the user that transmitted the query. For example, the server 102 can retrieve local ontologies 145 on a similar network as the server 102 or retrieve other ontologies 146 on external networks over the Internet or another local network. A domain of each of the ontologies can relate to, for example, the location of the user, a job of the user, and an identification of the user. Based on the identified ontologies from the ontology knowledge base 112, the server 102 can retrieve one or more knowledge graphs based on the one or more retrieved ontologies. A knowledge graph can correspond to one or more ontologies stored in the ontology knowledge base 112. The one or more ontologies represent a structured and formatted dataset and a corresponding knowledge graph to the one or more ontologies illustrated the structured and formatted dataset in a visual, semantic network manner. The knowledge graph module 130 can adjust or modify a knowledge graph in real time depending on the adjustments made to the ontologies or to the knowledge graph itself.

The server 102 can also retrieve data previously generated by the MRaaS module 126 from the historical database 114. For example, the server 102 can retrieve data that was previously generated for responses previously received queries. The server 102 can utilize data from the historical database 114 if the server 102 determines that the current query received by the client device 104 matches or partially matches to a previously received query. For example, the server 102 may be able to provide a quick response to a query that matches to a previously received query. Alternatively, the server 102 can use the previously generated ontologies, knowledge graphs, and other data for generating a response to a query in the case that a query partially matches to a previous query. The server 102 can determine a match or a partial match based on a string comparison between one or more queries.

The server 102 can also retrieve one or more external documents 138 from external sources for generating a response to the query. In some implementations, based on the determined characteristics of the user and the identified ontologies, the server 102 can ingest one or more external documents for determining a response to the query. For example, the server 102 can process a textbook, journal, or online site using optical character recognition (OCR) techniques and ingest the digitized data, e.g., the OCR data from the external sources, and provide the digitized data to the MRaaS module 126. In other examples, the server 102 can process other unstructured sources, e.g., speeches, patient data, lectures, etc., process the data from the unstructured sources into a machine-readable format understood by the MRaaS module 126, e.g., digitized data, and provide the digitized data to the MRaaS module 126. In some implementations, the server 102 can use the digitized data to identify local ontologies 145 or other ontologies 146. In particular, if the digitized data indicates a particular topic, e.g., biology, that is not included in the ontology knowledge base 112, then the server 102 can retrieve an ontology for that particular topic from the local ontology 145 or other ontologies 146. The server 102 can also retrieve other ontologies that can be necessary to generate a response based on the entities, relationships, and profile identified from the query that were not found in the ontology knowledge base 112.

In some implementations, the server may communicate the data associated with the query through a REST API 124 to the MRaaS module 126. The REST API 124 can correspond to a software architectural style that enables the use of Hyper Text Transfer Protocol (HTTP) to call one or more functions of the MRaaS module 126. For example, the REST API 124 relies on statelessness, an ability to cache, and a uniform interface to ensure the system improves performance, scalability, simplicity, modifiability, visibility, portability, and reliability. The REST API 124 may be called by the following commands, for example: GET, POST, PUT, and DELETE.

In some implementations, the MRaaS module 126 may include one or more modules, such as ontology module 128, a knowledge graph module 130, an inference engine 132, and an explainability module 134. Within the MRaaS module 126, a knowledge representation and reasoning system 129 exists and the explainability module 134. The knowledge representation and reasoning system 129 includes the ontology module 128, the knowledge graph module 130, and the inference engine 132. Each of these modules can communicate with one another and communicate with one or more components external to the MRaaS module 126 and external to the server 102.

The ontology module 128 can receive the ontologies provided through the REST API 124 that were identified based on the determined characteristics of the user that transmitted the query from the client device 104. Next, the ontology module 128 can identify a subset of ontologies from the received ontologies based on the one or more terms and their corresponding meanings as provided in the query. Thus, the ontology module 128 may identify three ontologies from the ten received ontologies, for example. In this example, the ontology module 128 can identify a heart disease ontology, an antibiotic resistance ontology, and an infectious disease ontology from the received ontologies based on the data in the entities 118, relationships 120, and the profile 122.

In response to identifying the ontologies based on the data in the query, the ontology module 128 can transmit the identified ontologies to the knowledge graph module 130. In this context, the knowledge graph module 130 can determine whether one or more previously generated knowledge graphs were instantiated from the identified ontologies provided by the ontology module 128. Alternatively, the knowledge graph module 130 may determine no previous knowledge graphs were instantiated from the identified ontologies, and then the knowledge graph module 130 can generate a new knowledge graph based on the received ontologies. The newly generated knowledge graph can correspond to a visual representation of a semantic network that illustrates the structural data stored by the received ontologies. In some implementations, the knowledge graph module 130 can generate or identify multiple knowledge graphs based on the received ontologies from the ontology module 128.

In response to the knowledge graph module 130 identifying or generating one or more knowledge graphs from the received ontologies, the knowledge graph module 130 provides the identified or generated one or more knowledge graphs to the inference engine 132. In some implementations, the inference engine 132 can receive the one or more knowledge graphs from the knowledge graph module 130 and traverse the knowledge graph for one or more responses to the provided query. Moreover, the inference engine 132, using forward chaining reasoning, traverses or searches through the knowledge graph to identify one or more conclusions or responses to the query based on the data identified in the query. The inference engine 132 can scan through the knowledge graph in different directions until one or more end nodes are identified or until a confidence level for a response at a particular node is met. The inference engine 132 can traverse through the knowledge graph by comparing entities and relationships represented by nodes and edges, respectively, compare to the data in the entities 118 and the relationships 120, for example.

In response to the inference engine 132 identifying one or more nodes from the knowledge graph that correspond to the results or responses of the query, the inference engine 132 can provide data to various components within and external to the MRaaS module 126. For example, the inference engine 132 can transmit query results to both the explainability module 134 and to the REST API 124 to be subsequently provided to the client device 104. Additionally, the inference engine 132 can provide inferred knowledge to the ontology module 128. In some examples, the inference engine 132 may determine one or more rules and instruct the ontology module 128 and knowledge graph module 130 to update an ontology and a corresponding new knowledge graph based on the implicit knowledge discovered from the inference engine results.

In some implementations, the explainability module 134 can receive the query results from the inference engine 132 and generate a path traversed by the inference engine 132 through the knowledge graph. The explainability module 134 can generate a path or trail illustrated in a visual graph or described in a structured document, to name a few examples. By generating the path traversed by the inference engine 132, a user can review the logic followed by the inference engine to determine the results or response of the query. The user can then indicate whether the logic is correct or issue feedback that can be used to improve the inference engine 132's (and other components within the MRaaS module 126) determination of query results. If the explainability module 134 determines that feedback is requested from the user that transmitted the query, the explainability module 134 can include data that represents feedback along with the data illustrating the traversal path, and provide both of those to the REST API 124.

In some implementations, the inference engine 132 and the explainability module 134 can provide both of their corresponding results to the REST API 124. In particular, the inference engine 132 can provide the query results to the REST API 124 and the explainability module 134 can provide data indicating the path taken by the inference engine 132 to the REST API 124. Then, the server 102 can provide both the query results and the data representing the path traversed by the inference engine 132 to derive at the query results to the client device 104.

In some implementations, in response to the server 102 providing the results and the data representing the path traversed, the server 102 may receive additional responses from the client device 104. For example, the additional responses may correspond to feedback from the provided search results. In particular, the client device 104 may display the results of the query and the data representing the path traversed to identify the results in a user interface (UI).

A user, such as user 103, may be able to interact with the UI of the client device 104 to view the results and report on the data representing the path traversed. For example, the user 103 can view each of the results or response to the query by selecting and opening the results. The results may include, for example: a document, a link to a document in a database local to the server 102, a link to a document external to the server 102, such as over the Internet, a snippet of information clipped from a document, a textbook, or a journal, and can also include media, such as images, videos, and/or audio files.

The data representing the path traversed can be illustrated on the UI of client device 104 as an interactive graph, an interactive structured document, or another form of GUI interaction. A user, such as user 103, may select one or more portions of the traversed path through the knowledge graph to identify a component of the knowledge graph. For example, the user 103 may be able to select a node or an edge along the traversed path of the knowledge graph and view its contents. A selected node may reveal the value of the node, e.g., an entity such as "Pericardial Aortic valve". Additionally, a selected edge between one or more nodes may reveal the value of the edge, e.g., a relationship such as "inversion". The GUI of the client device 104 may display the value of either the edge or the node in a separate window on the display.

If the user deems a portion of the traversed path to be inaccurate, e.g., the inference engine 132 made an incorrect determination when traversing from one node to another node, the user can interact with that portion of the traversed path on the GUI and indicate that that portion was determined in error. For example, the user may select a node or an edge of the traversed path, and select a button that indicates this was determined in error. In response, the user can also select a correction to transmit to the server. The correction may be, for example, another node should have been included in the traversed path, a different path should have been determined, or a different edge should have been traversed. In some examples, if the user determines that the knowledge graph's corresponding node is incorrect, the user can indicate that the ontologies were incorrectly determined and local ontologies can be updated with new knowledge. Since knowledge graph is a visual representation of the one or more ontologies, a change to the underlying ontology would change the architecture of the corresponding knowledge graph.

In some implementations, the data representing the path traversed can also include one or more questions that focuses the user's attention on the determined path. For example, the questions can include "Is this portion of the path correct?", "Does this path provide the requested results?", or "Do you have any recommendations to improve the determination of results?" The user can interact with the GUI to respond appropriately, such as, adjusting the terms of a query, adjust connections between nodes, adjust the traversed path, and adjust the results. In response to the user indicating the feedback, the client device 104 can provide the previous query along with the feedback to the server 102 for further processing. The server 102 can perform processes similar to processes performed for stages (A) through (F) with the additional processes of updating based on the feedback.

In some implementations, the server 102 can receive the feedback and retrieve data from the historical database 114 that matches to the query 106. In particular, the data from the historical database 114 that matches to the query 106 can include data associated with the query 106—the previously determined entities 118, relationships 120, profile 122, the previously retrieved ontologies, and the previously generated knowledge graphs. Then, the server 102 can apply the feedback to the previously retrieved data. For example, if the entities 118, relationships 120, or the one or more profiles 122 request updates, then the server 102 can adjust those components to reflect the updates. In response to updating those components, the server 102 can provide those reflected updates to the MRaaS module 126 to generate additional results.

In some implementations, if the feedback was directed towards components within the MRaaS module 126, then the server 102 can instruct the MRaaS module 126 to adjust the components based on the feedback. In particular, the server 102 can provide the feedback through the API 124 to the MRaaS module 126. The feedback may indicate to the MRaaS module 126, for example, to set certain parameters for selecting the subset of ontologies, instantiate the knowledge graphs with the subset of ontologies and ensure certain connections exist between one or more nodes, and when determining the results from the traversed path, ensure the inference engine 132 follows set rules when traversing the path in the knowledge graph, to name a few examples. Other feedback applications are also possible.

In response to generating the MRaaS module 126 generating new query results and data indicating a path traversed by the inference engine 132 to identify the new query results based on the feedback, the MRaaS module 126 can provide the new query results and the data indicating the path traversed to the client device. The server 102 may indicate to the client device 104 that the latest results include the response to the query and the path traversed based on the feedback provided by the user 103. At such time, the user 103 can confirm whether the new results are correct or to provide additional feedback.

In some implementations, the server 102 can apply results derived for one user's query to another user's query. For example, if the server 102 determines that the request from user 103, for example, is similar to a request provided by another user, the server 102 can apply the learned knowledge, e.g., the results generated from user 103's results, and generate similar results to provide to the other user and to other users. Generally, the components within the MRaaS module 126 can continuously learn to become more accurate, autonomous, knowledgeable, and provide responses that are more specific as more users provide queries to the server 102.

Figure 1C:
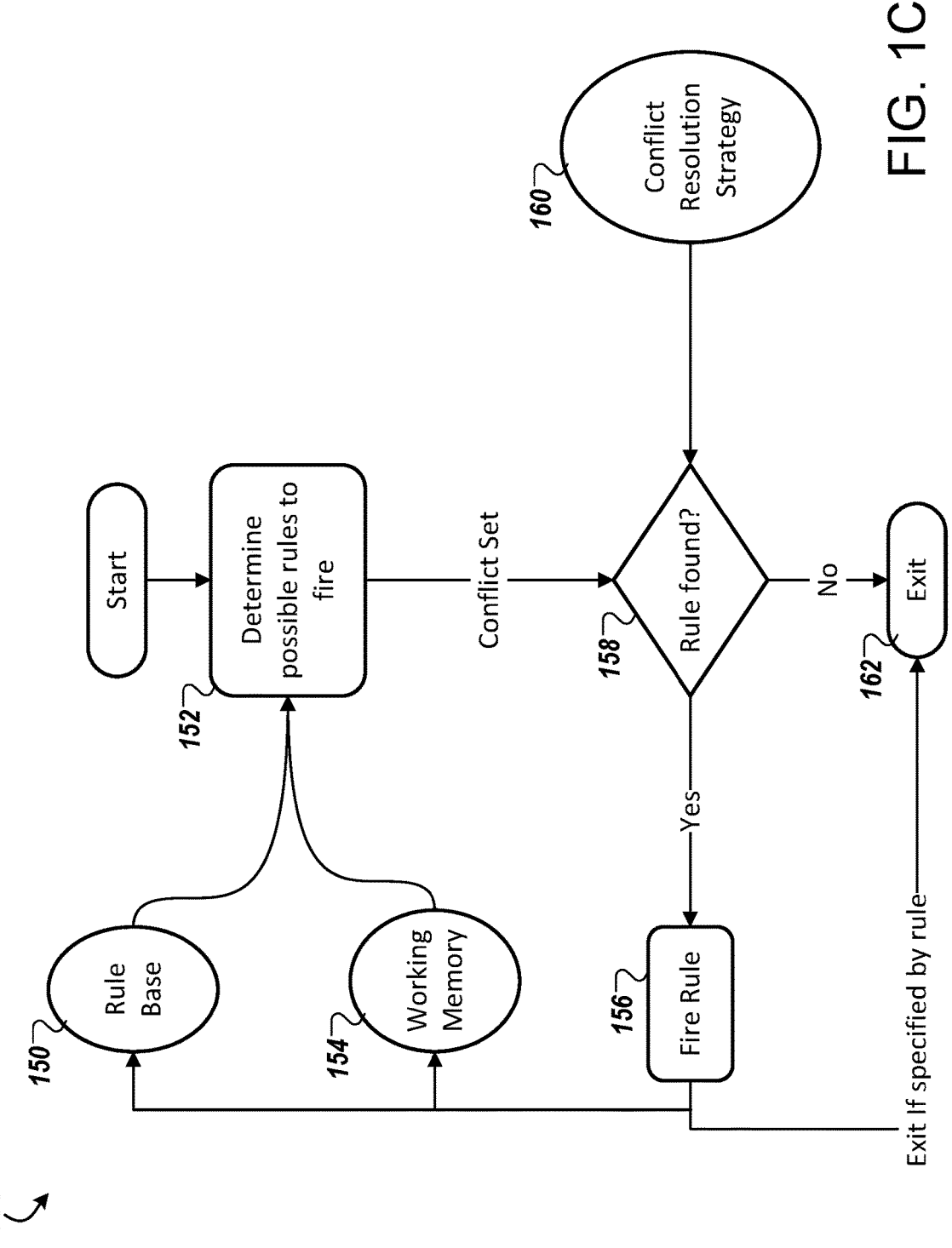
FIG. 1C is a block diagram that illustrates an example of a flow chart for an implementation of an inference engine.

FIG. 1C is a block diagram that illustrates an example of a flow chart 105 for an implementation of an inference engine. The flow chart 105 illustrates how inference engine 132 from FIG. 1A and FIG. 1B, for example, can traverse a knowledge graph for one or more responses to a provided query. As previously mentioned, the inference engine can rely on forward chaining reasoning to traverse or search through a knowledge graph to identify one or more conclusions or responses to the query based on the data identified in the query.

Generally, the inference engine relies on forward chaining and uses inference rules to extract data from available data until a goal is reached. More specifically, the inference engine uses forward chaining to search the inference rules until a rule is found where an antecedent, e.g., an IF clause, is known to be true. When the inference engine finds a rule where the antecedent is known to be true, the inference engine can conclude or infer the consequent, e.g., a THEN clause, is to be added, resulting in the addition of new information, e.g., the data from the THEN clause, to its dataset. In other words, the inference engine starts with facts or available data and applies rules to the data to find all possible conclusions. Therefore, the inference can use what is known as a data driven approach in an iterative manner.

In a forward chaining system, during analysis, information collected is added to the working memory 154. Information added to the working memory 154 can result in rules in the ontology knowledge base becoming ready to fire. A rule that can fire is a rule where all conditions attached to that rule are known to be true. If all conditions for that rule are true, then the advice from the rule can be generated. For example, in a large system of rules, at any one moment in time there may exist a series of rules that are ready to fire. The inference engine can use a conflict resolution strategy 160 to determine which rule should fire first. The inference engine can identify a number of rules which can fire at any time, which are more formally known as the conflict set.

In some implementations, the inference engine can utilize the conflict resolution strategy 160 to make the decision as to which rule should be fired first. The conflict resolution strategy 160 can rely on a variety of strategies. In one example, the inference engine can use rule ordering of a conflict resolution strategy 160. The rule ordering involves a first come, first serve methodology, which means the rule fired is the first rule in a conflict set. For example, if the conflict set contains rules 2, 5, 7, and 9, then the inference engine fires rule 2 first.

In another example, the inference engine can utilize a recency strategy. In a recency strategy, the inference engine can fire the rules which use the data added most recently to the working memory but not to the ontology knowledge base. For example, rule 1 can indicate: IF A and B, THEN C; rule 2 can indicate: IF D and E, THEN F; rule 3 can indicate: IF G and H, THEN I. If the inference engine determines the contents of the working memory include B, A, H, G, E, and D in order, with D as the most recent addition, then rule 2 will fire first, as D and E are the most recent additions.

In another example, the inference engine can utilize a specificity strategy. In a specificity strategy, the inference engine can fire the rule with the most conditions attached first. For example, rule 1 can indicate: IF A and B, then C; rule 2 can indicate: IF D and E and F, then G. In this example, the inference engine can fire rule 2 first because rule 2 includes three conditions attached as opposed to the two conditions attached in rule 1.

Additionally or alternatively, the inference can also utilize a refractoriness strategy. In a refractoriness strategy, the inference engine can prevent any rule that has already fired from firing again. If the inference engine does not employ the refractoriness strategy, then the inference engine may fire the same rule repeatedly, which can cause an infinite loop in the system. Once a rule has been fired, the inference engine can remove a rule permanently from the conflict set.

For example, as illustrated in flow chart 105, the inference engine initiates in block 152 by determining possible rules to fire. The inference engine identifies one or more rules from the rule base 150 and acquires available data from the working memory 154. Specifically, the inference engine examines the rules from the rule base 150 to find a rule who's IF clause is satisfied by the current contents of data available in the working memory 154, as illustrated by the decision block 158. The inference engine obtains data from the conflict resolution strategy 160 to determine whether the rule is found in the dataset. If the inference engine determines a rule is found, then the inference engine in block 156 fires the rule by adding the facts that are specified in the rules THEN clause to the working memory 154 and the rule base 150. If not, then the inference engine exits the rule in 162 for the IF clause and acquires the next rule. The inference engine repeats this iterative process until no rules have satisfied IF clauses for the dataset.

Figure 2A:
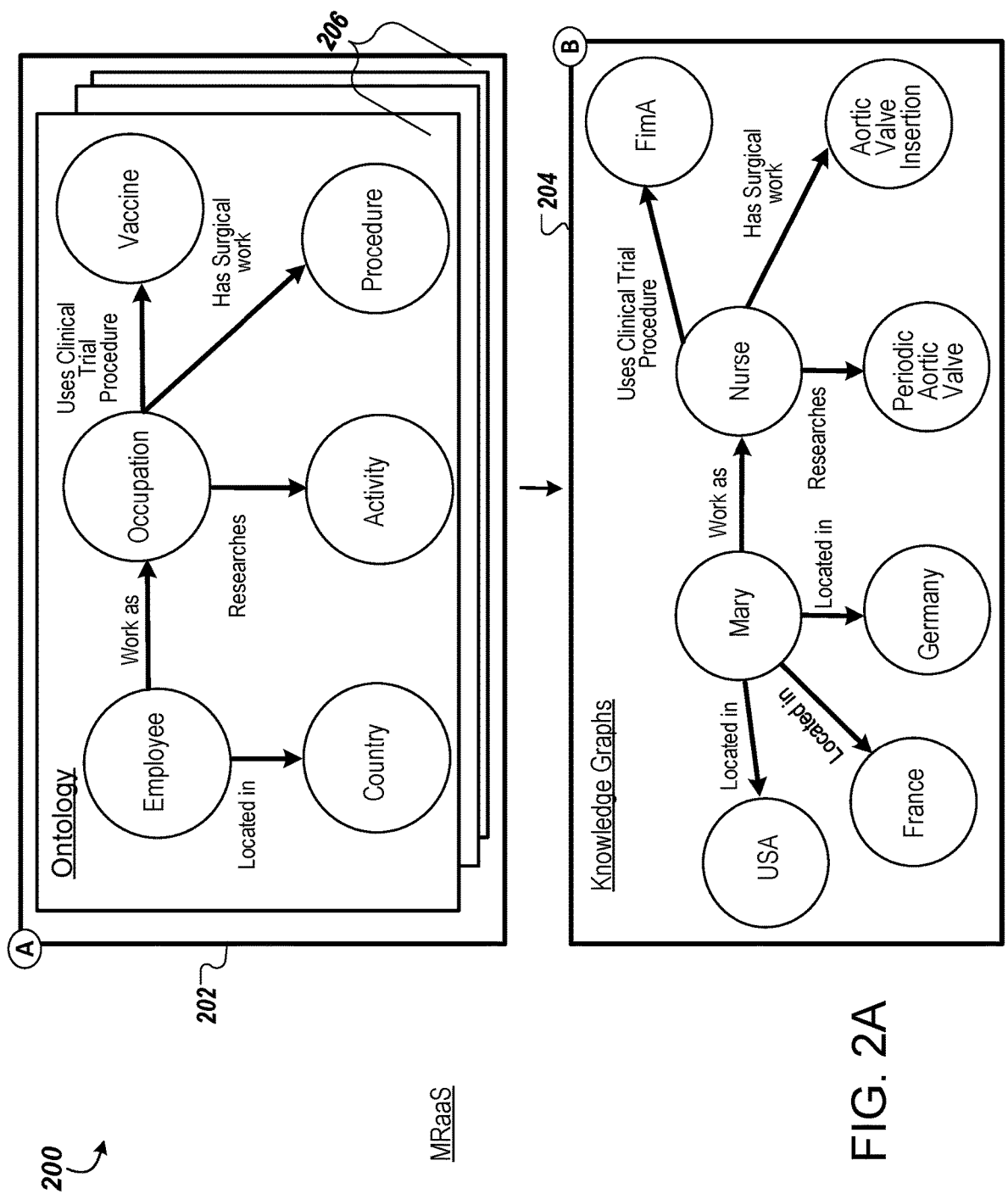
FIG. 2A is a block diagram that illustrates an example of ontologies and knowledge graphs within the MRaaS module.

FIG. 2A is a block diagram 200 that illustrates an example of ontologies and knowledge graphs within the MRaaS module. In particular, the block diagram 200 illustrates the ontology module 202 and the knowledge graph module 204. The ontology module 202 can include a plurality of ontologies 206 and the knowledge graph module 204 can illustrate a knowledge graph that is instantiated by the plurality of ontologies 206. FIG. 2A illustrates various operations in stages (A) through (B) which may be performed in the sequence indicated or another sequence.

During stage (A), the ontology module 202 can identify the subset of ontologies, e.g., the plurality of ontologies 206, from the received ontologies. One exemplar ontology from the plurality of ontologies can be seen in the FIG. 2A. The exemplar ontology can include a template for inserted data. For example, the first ontology illustrates the following information about an employee. The employee can be located in a particular country, e.g., Mary is located in Germany. The employee, e.g., Mary, can work at a particular occupation. For example, Mary works as a nurse.

At the occupation, the ontology illustrates the employee can perform various activities, such as researching an activity, using a clinical trial procedure for a vaccine, and performs surgical work for a procedure. For example, as a nurse, Mary can research one or more medical activities, e.g., heart monitoring, aortic valves insertion, aortic valve insertion in reverse, study endocarditis, infections, medical procedures, asthma, and biomedicine. Continuing with Mary as a nurse, Mary can use a clinical trial procedure for studying a flu vaccine. In another example, Mary has surgical work for an orthopedic procedure as a nurse. The ontology can also include multiple activities at the occupation, such as, medical advice, surgical coordination, topical medical creams, and monitoring infections, to name a few examples.

During stage (B), the knowledge graph module 204 generates or identifies a visual representation of the plurality of ontologies 206 in a semantic network known as a knowledge graph. The knowledge graph illustrated in FIG. 2A can illustrate, for example, that Mary can be located in USA, France, or Germany. Additionally, the knowledge graph can illustrate that Mary can work as a nurse. As a nurse, Mary can research periocardic aortic valve, can use a clinical trial procedure to investigate a FimA vaccine, and performs surgical work in aortic valve insertion.

Figure 2B:
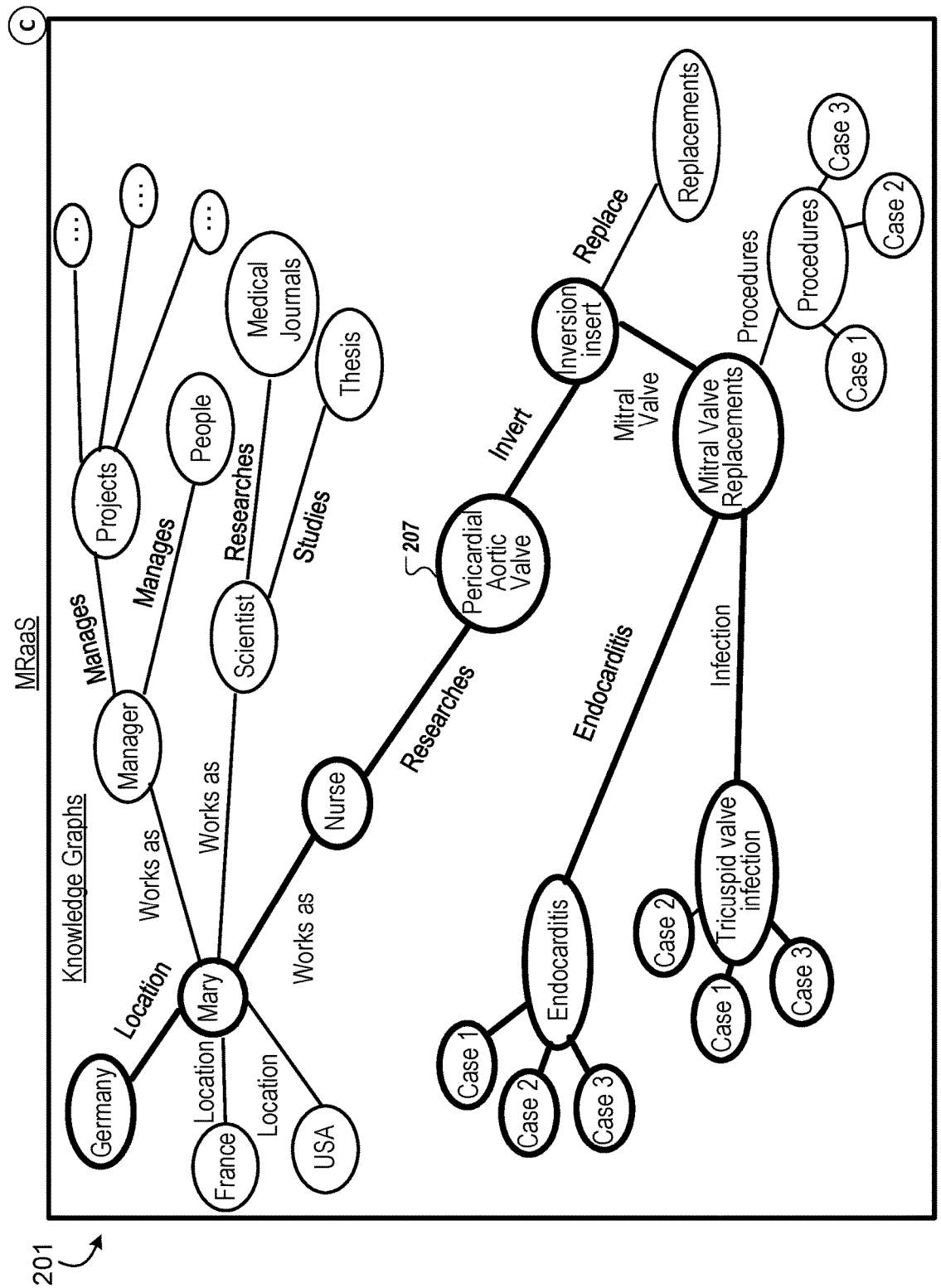
FIG. 2B is a block diagram that illustrates an example of a system for receiving a response and providing feedback to results of a query.

FIG. 2B is a block diagram 201 that illustrates an example of a system for traversing a knowledge graph within the MRaaS module. The block diagram 201 is a continuation of block diagram 200. Block diagram 200 illustrates stages (A) and (B) and block diagram 201 illustrates stage (C). Within the block diagram 201, the inference engine can traverse the knowledge graph and determine a path based on the data provided from the query.

During stage (C), the inference engine can traverse a path 207 to identify results of a query or a response to the query. For example, the inference engine can identify a traversed path 207 that indicates the node labeled "Mary" is located in Germany, works as a nurse, and performs research to identify various cases, e.g., the cases 1, 2, and 3 connected to a node labeled "Endocarditis" and cases 1, 2, and 3 connected to a node labeled "tricuspid valve infection". The MRaaS module can provide both sets of cases to the REST API to provide the results back to the client device. Additionally, the inference engine can provide the both sets of cases 1, 2, and 3 to the explainability module. The explainability module can identify the traversed path as path 207, and provide data representing the traversed path to the client device that provided the query.

FIG. 2C is a block diagram that illustrates an example of a system 203 for receiving a response and providing feedback to results of a query. System 203 is a continuation of the processes that occurred in the block diagrams 200 and 201. FIG. 2C illustrates various operations in stages (D) through (E) which may be performed in the sequence indicated or another sequence.

During stage (D), the server 222 can transmit the results 218 to the client device 210 over a network 224. The results 218 can include responses 218*a* to the query and the data 218*b* indicated by the explainability module illustrating the path traversed through the knowledge graph to identify responses 213*a*. The client device 210 can receive the results 218 and display the results 218 in a GUI of the client device 210. For example, the GUI may be separated into three different components: a first GUI 212 for illustrating the query, a second GUI 214 for illustrating the results of the query developed by the MRaaS module, and a third GUI 216 for illustrating the data 218*b* provided by the explainability module that shows a path that is reverse of the path traversed through the knowledge graph generated by the inference engine path to identify the results 218*a*. For example, the GUI 216 illustrates the cases identified by the inference engine and illustrates a reverse path back to the user Mary and her corresponding location.

During stage (E), the user 208 may interact with one or more of the GUIs, e.g., GUIs 212, 214, and 216, to review the results 218*a* and/or provide feedback on the results 218*a* or data 218*b* provided by the explainability module. In particular, and as illustrated in system 203, the user 208 can provide feedback 226 to adjust the query. The feedback 226 may include, among other things, the textual feedback 228, graphical feedback, the query the feedback 226 is associated with, data identifying the user 208, and data identifying the client device 210. For example, the user 208 can indicate to the server 222 to adjust the query to include textual feedback 228 that recites "Change to 'heart failure occurring' instead of 'endocarditis'". The server 222 can receive the feedback 226 and generate new results to provide to the client device 210 of user 208.

Figure 3:
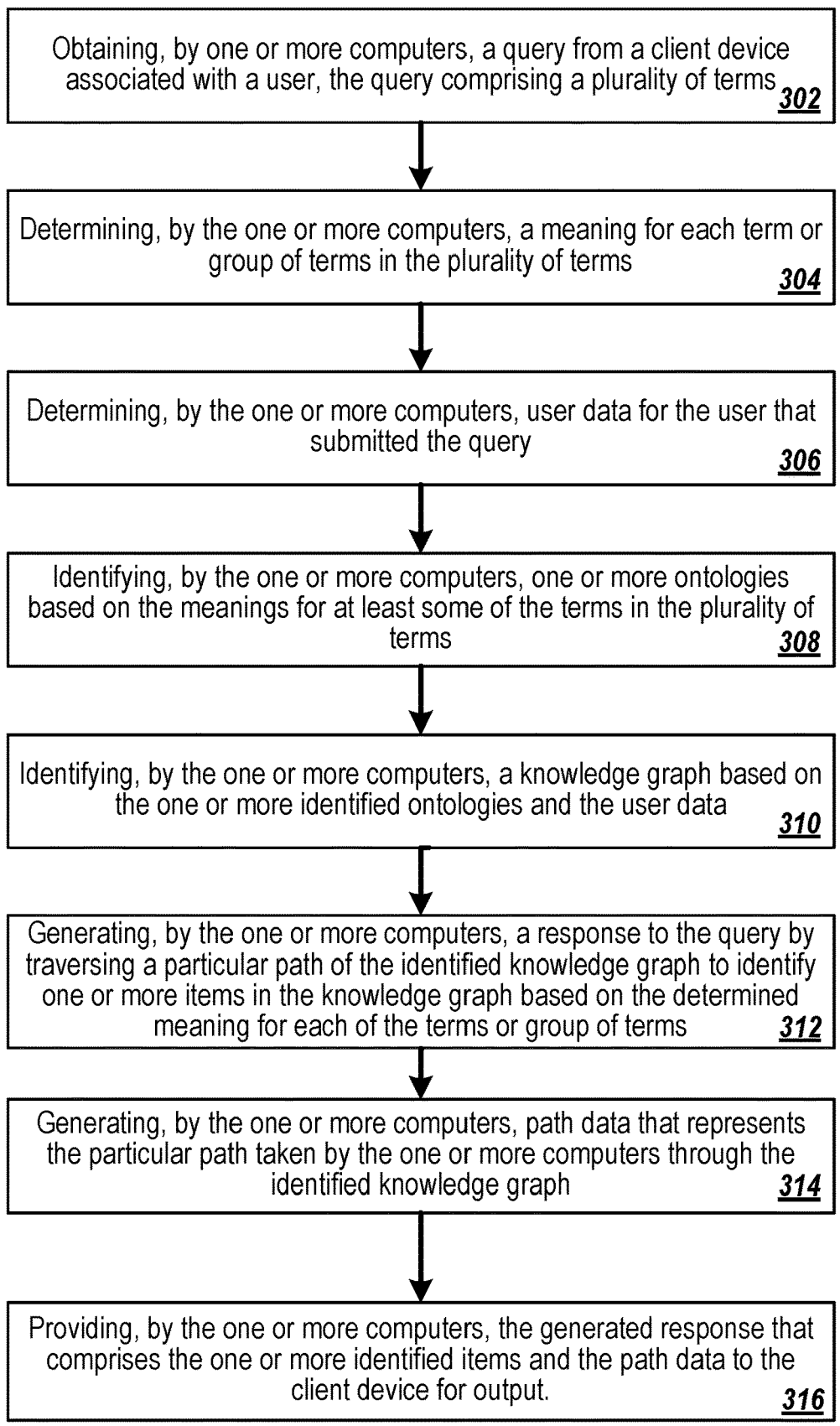
FIG. 3 is a flow diagram that illustrates an example of a process for generating a response to a query using Machine Reasoning as a Service (MRaaS).

FIG. 3 is a flow diagram that illustrates an example of a process 300 for generating a response to a query using Machine Reasoning as a Service (MRaaS). The process 300 can be performed, for example, by the server 102, which can include one or more computers, illustrated in FIGS. 1A and 1B.

The server can obtain a query from a client device associated with a user, the query including a plurality of terms (302). The query can correspond to a complex medical topic, for example. The user can enter the query to the client device and the client device can transmit the query to the server. The query can also include additional information about the user that entered the query, e.g., the user's job title, a characterization of the user's job responsibilities, a job title at the particular location, or a job category.

The server can determine a meaning for each term or group of terms in the plurality of terms (304). The server can receive the query and parse the one or more terms in the query into separate terms. Based on the separate terms, the server can identify entities and relationships from each of the separate terms, where the entities can correspond to clinical terms and the relations can correspond to clinical actions performed by or for the entities. The server can use an NLP module to identify entities and relationships from the parsed terms of the query.

The server can determine user data for the user that submitted the query (306). Based on the query, the server can identify a location of the user that submitted the query, a job location of the user, and a current job position of the user. In some implementations, the server can generate a user profile of the user based on the determined user data. For example, the user profile of the user can indicate that the user is John, who is a doctor currently located in Switzerland, but that John's hometown is in London.

The server can identify one or more ontologies based on the meanings for at least some of the terms in the plurality of terms (308). For example, the server can access an ontology knowledge base that stores a plurality of ontologies, each ontology in the plurality of ontologies built using historical medical data that include at least one of previous clinical trial data, clinical journals, biology data, life sciences data, genetic data, disease data, and pharmacological data, and the historical medical data is stored in each of the ontologies in a structured manner. The server can then retrieve one or more of the ontologies using the determined characteristics of the user, e.g., user data, and some of the terms identified from the provided query.

Once the server has identified and retrieved the ontologies based on the determined characteristics of the user, the MRaaS module of the server can identify a subset of ontologies from the received ontologies based on the terms identified by entities, the relationships, and a user profile. For example, an ontology module of the MRaaS module can perform string matching, partial matching, and other matching function, using the entities, the relationships, and the user profile to identify ontologies that are relevant to the query.

The server can identify a knowledge graph based on the one or more identified ontologies and the user data (310). In some implementations, the server can identify a knowledge graph from a plurality of stored knowledge graphs, each stored knowledge graph of the plurality of stored knowledge graphs connecting entities and corresponding relationships. The server can identify a knowledge graph from the plurality of stored knowledge graphs based on a match to the subset of identified ontologies. For example, a knowledge graph module of the server can determine whether a stored knowledge graph was instantiated with ontologies that match to the identified subset of ontologies, and if so, the knowledge graph module can retrieve that particular knowledge graph for usage. Once the knowledge graph module identifies a knowledge graph for traversing, the knowledge graph module can transmit data representing the identified knowledge graph to the inference engine for processing the data in the identified knowledge graph and generating results for the query.

The server can generate a response to the query by traversing a particular path of the identified knowledge graph to identify one or more items in the knowledge graph based on the determined meaning for each of the terms or group of terms (312). For example, the inference engine can use the identified knowledge graph to traverse the particular path of the identified knowledge graph based on the determined meaning for each term from the query and by accessing one or more items located an end of the particular path. For instance, the inference engine can traverse, search, or review the identified knowledge graph to induce or determine a particular conclusion. The inference engine can traverse the identified knowledge graph to determine the conclusion based on the terms or group of terms and their corresponding meaning from the received query. The knowledge graph can match the meaning for each term from the query to entities and relationships found in the identified knowledge graph. For example, the inference engine can hop from one node to another node along an edge that connects the two nodes when the data representing these corresponding components match to the entities, relationships, and profile to a particular degree. The inference engine may determine that the entities and relationships represented by the nodes and edges in the knowledge graph, respectively, match to the entities and relationship based on statistics, probabilities, or other factors. The inference engine can repeat this iterative traversal process until one or more nodes are reached no further connecting edges. In response, the inference engine can return the values described by these nodes.

In some implementations, the inference engine can provide the determined results of the query to an explainability module. Similarly, the inference engine can transfer data inferred from traversal of the knowledge graph to the ontology module. The data inferred from traversal of the knowledge graph can include the following: (i) results identified by the inference engine, e.g., the nodes where traversal ended; (ii) path data that indicates the path taken by the inference engine through the knowledge graph; and, (iii) the statistical values illustrating the matches between the entities, relationships, and profile and the data in the knowledge graph. The ontology module can receive and store the inferred data associated with data from the query so the next time the server receives a similar query from the user with similar parameters, the ontology module can provide a similar response to the query without having to process a corresponding knowledge graph, as the results would be readily available from a previously submitted query.

The server can generate path data that represents the particular path taken by the server through the identified knowledge graph (314). The explainability module can generate the path taken through the knowledge graph to identify the one or more conclusions. The explainability module can generate data that illustrates a trail or path traversed through the knowledge graph of how the inference engine moved from one node to the next node to identify results based on the entities, the relationships, and the profile extracted from the query. The explainability module can then provide the generated data of how the results were determined through the API to be provided to the client device. In some cases, the explainability module can provide a visual path that is readable and understood by a human. This data can include a visual graph showing connecting nodes and edges and a highlighted or bolded pathway through the knowledge graph from start to finish. The data can also be illustrated in bulleted, paragraphed, or some other structural documented form that describes how the inference engine traversed the knowledge graph.

In some implementations, the explainability module can show a reverse path of the path taken by the inference engine. The reverse path can correspond to a path that begins where the inference engine path ends and ends where the inference engine path began. The explainability module can provide the reverse path to a reviewing user so the user can see how the MRaaS module arrived at the conclusions. In this sense, the user can provide feedback if the user does not agree with the logic of the path or reverse path provided by the server to the client device.

The server can provide the generated response that comprises the one or more identified items and the path data to the client device for output (316). For example, the server can provide the generated response to the query, e.g., the one or more identified items, and the path tracked and taken by the server through the knowledge graph, to the client device over a network. In response to the server providing the generated responses to the client device for output, the server can receive an update from the client device that includes one or more modifications to the one or more identified local ontologies and to the identified knowledge graph. The server can modify the one or more identified local ontologies or the identified knowledge graph based on the update provided by the client device using one or more modifications. The server can also make modifications to other components and algorithms within the MRaaS module that include, for example, inferred knowledge and traversal knowledge.

Figure 4:
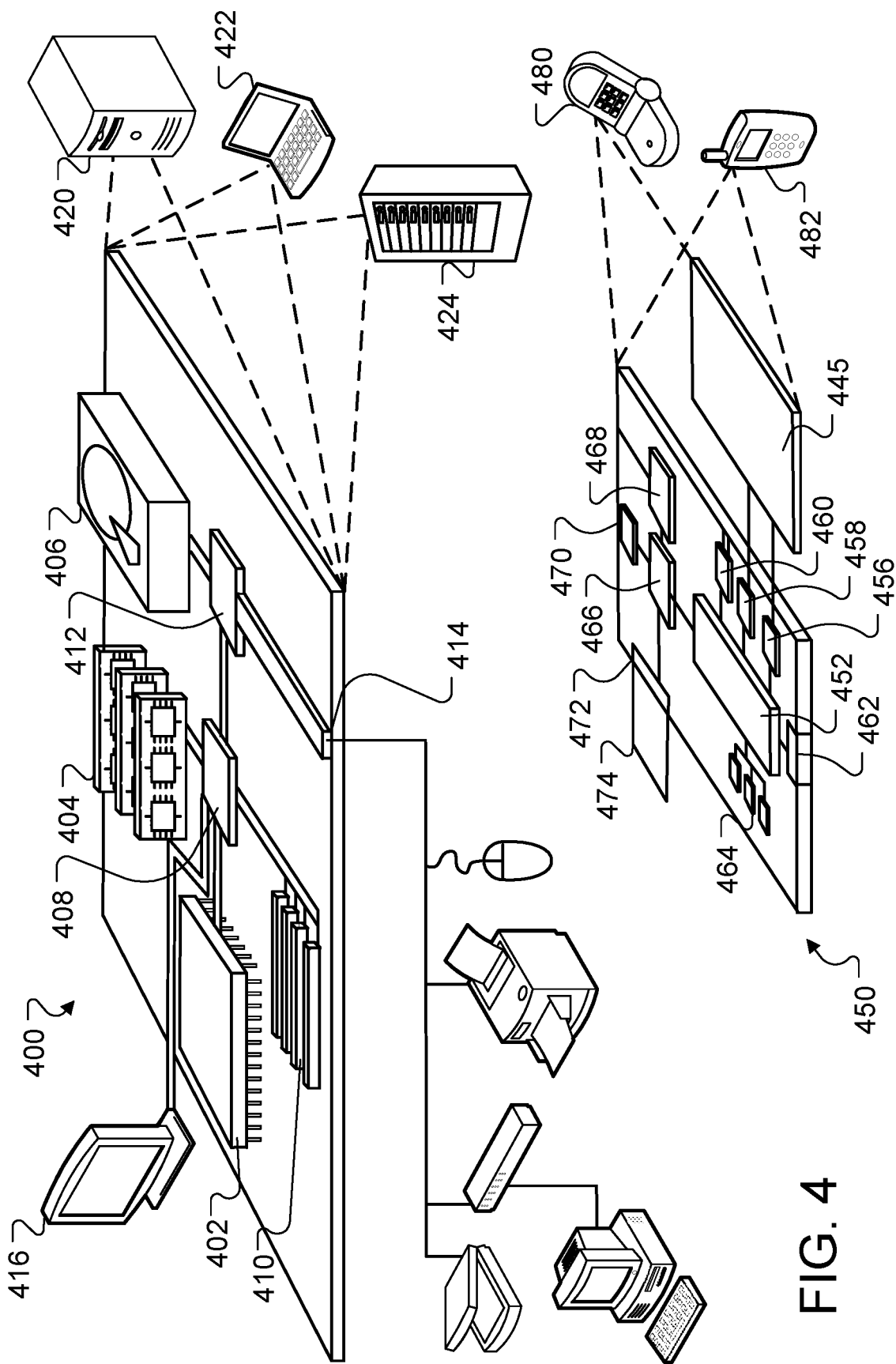
FIG. 4 shows a block diagram of a computing system that can be used in connection with methods described in this document.

FIG. 4 is a block diagram of computing devices 400, 450 that may be used to implement the systems and methods described in this document, as either a client or as a server or multiple servers. Computing device 400 and 450 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations described and/or claimed in this document.

Computing device 400 includes a processor 402, memory 404, a storage device 406, a high-speed interface 408 connecting to memory 404 and high-speed expansion ports 410, and a low speed interface 412 connecting to low speed bus 414 and storage device 406. Each of the components 402, 404, 406, 408, 410, and 412, are interconnected using various busses, and may be mounted on a common motherboard or in other manners as appropriate. The processor 402 can process instructions for execution within the computing device 400, including instructions stored in the memory 404 or on the storage device 406 to display graphical information for a GUI on an external input/output device, such as display 416 coupled to high speed interface 408. In other implementations, multiple processors and/or multiple buses may be used, as appropriate, along with multiple memories and types of memory. Also, multiple computing devices 400 may be connected, with each device providing portions of the necessary operations, e.g., as a server bank, a group of blade servers, or a multi-processor system.

The memory 404 stores information within the computing device 400. In one implementation, the memory 404 is a computer-readable medium. In one implementation, the memory 404 is a volatile memory unit or units. In another implementation, the memory 404 is a non-volatile memory unit or units.

The storage device 406 is capable of providing mass storage for the computing device 400. In one implementation, the storage device 406 is a computer-readable medium. In various different implementations, the storage device 406 may be a floppy disk device, a hard disk device, an optical disk device, or a tape device, a flash memory or other similar solid-state memory device, or an array of devices, including devices in a storage area network or other configurations. In one implementation, a computer program product is tangibly embodied in an information carrier. The computer program product contains instructions that, when executed, perform one or more methods, such as those described above. The information carrier is a computer- or machine-readable medium, such as the memory 404, the storage device 406, or memory on processor 402.

The high-speed controller 408 manages bandwidth-intensive operations for the computing device 400, while the low speed controller 412 manages lower bandwidth-intensive operations. Such allocation of duties is exemplary only. In one implementation, the high-speed controller 408 is coupled to memory 404, display 416, e.g., through a graphics processor or accelerator, and to high-speed expansion ports 410, which may accept various expansion cards (not shown). In the implementation, low-speed controller 412 is coupled to storage device 406 and low-speed expansion port 414. The low-speed expansion port, which may include various communication ports, e.g., USB, Bluetooth, Ethernet, wireless Ethernet, may be coupled to one or more input/output devices, such as a keyboard, a pointing device, a scanner, or a networking device such as a switch or router, e.g., through a network adapter.

The computing device 400 may be implemented in a number of different forms, as shown in the figure. For example, it may be implemented as a standard server 420, or multiple times in a group of such servers. It may also be implemented as part of a rack server system 424. In addition, it may be implemented in a personal computer such as a laptop computer 422. Alternatively, components from computing device 400 may be combined with other components in a mobile device (not shown), such as device 450. Each of such devices may contain one or more of computing device 400, 450, and an entire system may be made up of multiple computing devices 400, 450 communicating with each other.

Computing device 450 includes a processor 452, memory 464, an input/output device such as a display 454, a communication interface 466, and a transceiver 468, among other components. The device 450 may also be provided with a storage device, such as a microdrive or other device, to provide additional storage. Each of the components 450, 452, 464, 454, 466, and 468, are interconnected using various buses, and several of the components may be mounted on a common motherboard or in other manners as appropriate.

The processor 452 can process instructions for execution within the computing device 450, including instructions stored in the memory 464. The processor may also include separate analog and digital processors. The processor may provide, for example, for coordination of the other components of the device 450, such as control of user interfaces, applications run by device 450, and wireless communication by device 450.

Processor 452 may communicate with a user through control interface 458 and display interface 456 coupled to a display 454. The display 454 may be, for example, a TFT LCD display or an OLED display, or other appropriate display technology. The display interface 456 may include appropriate circuitry for driving the display 454 to present graphical and other information to a user. The control interface 458 may receive commands from a user and convert them for submission to the processor 452. In addition, an external interface 462 may be provided in communication with processor 452, so as to enable near area communication of device 450 with other devices. External interface 462 may provide, for example, for wired communication, e.g., via a docking procedure, or for wireless communication, e.g., via Bluetooth or other such technologies.

The memory 464 stores information within the computing device 450. In one implementation, the memory 464 is a computer-readable medium. In one implementation, the memory 464 is a volatile memory unit or units. In another implementation, the memory 464 is a non-volatile memory unit or units. Expansion memory 474 may also be provided and connected to device 450 through expansion interface 472, which may include, for example, a SIMM card interface. Such expansion memory 474 may provide extra storage space for device 450, or may also store applications or other information for device 450. Specifically, expansion memory 474 may include instructions to carry out or supplement the processes described above, and may include secure information also. Thus, for example, expansion memory 474 may be provided as a security module for device 450, and may be programmed with instructions that permit secure use of device 450. In addition, secure applications may be provided via the SIMM cards, along with additional information, such as placing identifying information on the SIMM card in a non-hackable manner.

The memory may include for example, flash memory and/or MRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 464, expansion memory 474, or memory on processor 452.

Device 450 may communicate wirelessly through communication interface 466, which may include digital signal processing circuitry where necessary. Communication interface 466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 468. In addition, short-range communication may occur, such as using a Bluetooth, WiFi, or other such transceiver (not shown). In addition, GPS receiver module 470 may provide additional wireless data to device 450, which may be used as appropriate by applications running on device 450.

Device 450 may also communicate audibly using audio codec 460, which may receive spoken information from a user and convert it to usable digital information. Audio codec 460 may likewise generate audible sound for a user, such as through a speaker, e.g., in a handset of device 450. Such sound may include sound from voice telephone calls, may include recorded sound, e.g., voice messages, music files, etc., and may also include sound generated by applications operating on device 450.

The computing device 450 may be implemented in a number of different forms, as shown in the figure. For example, it may be implemented as a cellular telephone 480. It may also be implemented as part of a smartphone 482, personal digital assistant, or other similar mobile device.

Various implementations of the systems and techniques described here can be realized in digital electronic circuitry, integrated circuitry, specially designed ASICs, computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs, also known as programs, software, software applications or code, include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back-end component, e.g., as a data server, or that includes a middleware component such as an application server, or that includes a front-end component such as a client computer having a graphical user interface or a Web browser through which a user can interact with an implementation of the systems and techniques described here, or any combination of such back-end, middleware, or front-end components. The components of the system can be interconnected by any form or medium of digital data communication such as, a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In addition, certain data may be treated in one or more ways before it is stored or used, so that personally identifiable information is removed. For example, in some embodiments, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over what information is collected about the user, how that information is used, and what information is provided to the user.

A number of embodiments have been described. Nevertheless, it will be understood that various modifications may be made without departing from the spirit and scope of the invention. Accordingly, other embodiments are within the scope of the following claims. While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment.

Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, some processes depicted in the accompanying figures do not necessarily require the particular order shown, or sequential order, to achieve desirable results.

What is claimed is:

1. A computer-implemented method performed by one or more computers comprising:
    accessing, by the one or more computers, a knowledge graph based on data indicative of a user associated with a client device from which a query is received;
    traversing, by the one or more computers, a plurality of nodes and a plurality of edges in the accessed knowledge graph using data representing the received query, wherein the traversing comprises traversing a path including (i) a subset of the nodes that are associated with words corresponding to one or more words of the query and (ii) a subset of the edges that are associated with words corresponding to one or more words of the query;
    generating, by the one or more computers, a response to the query using data identified from the traversal of the accessed knowledge graph, wherein the generating comprises generating results of the traversed path, the results comprise (i) one or more nodes in the accessed knowledge graph where the traversal ended, (ii) data indicative of confidences of correspondences between the words of the query and the words associated with the nodes of the subset of nodes or the edges of the subset of edges; and
    providing, by the one or more computers and to the client device, the generated response.

2. The computer-implemented method of claim 1, wherein the received query comprises text requesting information for a medical topic and the data indicative of the user comprises identification information of the user.

3. The computer-implemented method of claim 2, wherein the identification information of the user comprises at least one of (i) a current location of the client device, (ii) a current job location of the user, and (iii) a current job position of the user.

4. The computer-implemented method of claim 2, wherein accessing the knowledge graph based on the data indicative of the user comprises:
    selecting, by the one or more computers, a subset of ontologies from one or more ontologies of an ontology knowledge base and at least some of the information for the medical topic of the query, the ontology knowledge base storing a plurality of ontologies, each ontology in the plurality of ontologies containing historical medical data stored in a structural manner,
    wherein the one or more ontologies are accessed using the data indicative of the user.

5. The computer-implemented method of claim 4, further comprising:
    identifying, by the one or more computers, a particular knowledge graph from a plurality of knowledge graphs based on data selected in the subset of ontologies, wherein the nodes of each knowledge graph represent corresponding entities and wherein the edges of each knowledge graph represent relationships between the entities; and
    providing, by the one or more computers, the identified knowledge graph to an inference engine for traversal, wherein accessing the knowledge graph based on data indicative of the user comprises accessing the identified knowledge graph.

6. The computer-implemented method of claim 2, wherein providing the generated response to the client device comprises providing, by the one or more computers and to the client device, (i) graphical illustrations representing the traversed path taken by the one or more computers through the accessed knowledge graph and (ii) the results of the traversed path.

7. A system comprising:
    one or more computers and one or more storage devices storing instructions that are configured, when executed by the one or more computers, to cause the one or more computers to perform operations comprising:
        accessing, by the one or more computers, a knowledge graph based on data indicative of a user associated with a client device from which a query is received;
        traversing, by the one or more computers, a plurality of nodes and a plurality of edges in the accessed knowledge graph using data representing the received query, wherein the traversing comprises traversing a path including (i) a subset of the nodes that are associated with words corresponding to one or more words of the query and (ii) a subset of the edges that are associated with words corresponding to one or more words of the query;
        generating, by the one or more computers, a response to the query using data identified from the traversal of the accessed knowledge graph, wherein the generating comprises generating results of the traversed path, the results comprise (i) one or more nodes in the accessed knowledge graph where the traversal ended, (ii) data indicative of confidences of correspondences between the words of the query and the words associated with the nodes of the subset of nodes or the edges of the subset of edges; and
        providing, by the one or more computers and to the client device, the generated response.

8. The system of claim 7, wherein the received query comprises text requesting information for a medical topic and the data indicative of the user comprises identification information of the user.

9. The system of claim 8, wherein the identification information of the user comprises at least one of (i) a current location of the client device, (ii) a current job location of the user, and (iii) a current job position of the user.

10. The system of claim 8, wherein accessing the knowledge graph based on the data indicative of the user comprises:
selecting, by the one or more computers, a subset of ontologies from one or more ontologies of an ontology knowledge base and at least some of the information for the medical topic of the query, the ontology knowledge base storing a plurality of ontologies, each ontology in the plurality of ontologies containing historical medical data stored in a structural manner,
wherein the one or more ontologies are accessed using the data indicative of the user.

11. The system of claim 10, further comprising:
identifying, by the one or more computers, a particular knowledge graph from a plurality of knowledge graphs based on data selected in the subset of ontologies, wherein the nodes of each knowledge graph represent corresponding entities and wherein the edges of each knowledge graph represent relationships between the entities; and
providing, by the one or more computers, the identified knowledge graph to an inference engine for traversal, wherein accessing the knowledge graph based on data indicative of the user comprises accessing the identified knowledge graph.

12. The system of claim 7, wherein providing the generated response to the client device comprises providing, by the one or more computers and to the client device, (i) graphical illustrations representing the traversed path taken by the one or more computers through the accessed knowledge graph and (ii) the results of the traversed path.

13. A non-transitory computer-readable medium storing software comprising instructions executable by one or more computers which, upon such execution, cause the one or more computers to perform operations comprising:
accessing, by the one or more computers, a knowledge graph based on data indicative of a user associated with a client device from which a query is received;
traversing, by the one or more computers, a plurality of nodes and a plurality of edges in the accessed knowledge graph using data representing the received query, wherein the traversing comprises traversing a path including (i) a subset of the nodes that are associated with words corresponding to one or more words of the query and (ii) a subset of the edges that are associated with words corresponding to one or more words of the query;
generating, by the one or more computers, a response to the query using data identified from the traversal of the accessed knowledge graph, wherein the generating comprises generating results of the traversed path, the results comprise (i) one or more nodes in the accessed knowledge graph where the traversal ended, (ii) data indicative of confidences of correspondences between the words of the query and the words associated with the nodes of the subset of nodes or the edges of the subset of edges; and
providing, by the one or more computers and to the client device, the generated response.

14. The non-transitory computer-readable medium of claim 13, wherein the received query comprises text requesting information for a medical topic and the data indicative of the user comprises identification information of the user.

15. The non-transitory computer-readable medium of claim 14, wherein the identification information of the user comprises at least one of (i) a current location of the client device, (ii) a current job location of the user, and (iii) a current job position of the user.

16. The non-transitory computer-readable medium of claim 14, wherein accessing the knowledge graph based on the data indicative of the user comprises:
selecting, by the one or more computers, a subset of ontologies from one or more ontologies of an ontology knowledge base and at least some of the information for the medical topic of the query, the ontology knowledge base storing a plurality of ontologies, each ontology in the plurality of ontologies containing historical medical data stored in a structural manner,
wherein the one or more ontologies are accessed using the data indicative of the user.

* * * * *

UNITED STATES PATENT AND TRADEMARK OFFICE
CERTIFICATE OF CORRECTION

PATENT NO. : 12,230,405 B1
APPLICATION NO. : 18/443857
DATED : February 18, 2025
INVENTOR(S) : Scott Josephson and Gary Shorter Page 1 of 1

It is certified that error appears in the above-identified patent and that said Letters Patent is hereby corrected as shown below:

In the Claims

Column 34, Line 32, Claim 6, delete "claim 2," and insert -- claim 1, --.

Signed and Sealed this
Third Day of June, 2025

Coke Morgan Stewart
*Acting Director of the United States Patent and Trademark Office*